United States Patent
Braae et al.

(10) Patent No.: US 12,241,115 B2
(45) Date of Patent: Mar. 4, 2025

(54) METHODS AND COMPOSITIONS FOR ENRICHING NUCLEIC ACIDS

(71) Applicant: ASKLEPIOS BIOPHARMACEUTICAL, INC., RTP, NC (US)

(72) Inventors: Anne Braae, Midlothian (GB); Juan Manuel Iglesias Gonzalez, Midlothian (GB); Joanna Critchley, Midlothian (GB); Michael Roberts, Midlothian (GB); Ross Fraser, Midlothian (GB)

(73) Assignee: ASKLEPIOS BIOPHARMACEUTICAL, INC., Research Triangle Park, NC (US)

( * ) Notice: Subject to any disclaimer, the term of this patent is extended or adjusted under 35 U.S.C. 154(b) by 921 days.

(21) Appl. No.: 16/970,838

(22) PCT Filed: Feb. 25, 2019

(86) PCT No.: PCT/GB2019/050500
§ 371 (c)(1),
(2) Date: Aug. 18, 2020

(87) PCT Pub. No.: WO2019/166784
PCT Pub. Date: Sep. 6, 2019

(65) Prior Publication Data
US 2021/0180111 A1 Jun. 17, 2021

(30) Foreign Application Priority Data
Feb. 28, 2018 (GB) ...................... 1803240

(51) Int. Cl.
*C12Q 1/6806* (2018.01)
*C12N 15/10* (2006.01)

(52) U.S. Cl.
CPC ....... *C12Q 1/6806* (2013.01); *C12N 15/1034* (2013.01); *C12Q 2521/325* (2013.01); *C12Q 2522/101* (2013.01); *C12Q 2525/204* (2013.01); *C12Q 2527/107* (2013.01); *C12Q 2537/159* (2013.01); *C12Q 2537/163* (2013.01)

(58) Field of Classification Search
None
See application file for complete search history.

(56) References Cited

U.S. PATENT DOCUMENTS

| 8,728,767 B2 | 5/2014 | Shapero | |
| 2017/0233764 A1* | 8/2017 | Young | C12N 9/93 |
| | | | 435/6.12 |

FOREIGN PATENT DOCUMENTS

| EP | 2976435 A1 | 1/2016 |
| EP | 2976435 B1 | 10/2017 |
| WO | 2009121550 A1 | 10/2009 |
| WO | 2016090344 A1 | 6/2016 |
| WO | 2016093838 A1 | 6/2016 |
| WO | 2016187583 A1 | 11/2016 |

OTHER PUBLICATIONS

Alberts B, Johnson A, Lewis J, et al. Molecular Biology of the Cell. 4th edition. New York: Garland Science; 2002. Isolating, Cloning, and Sequencing DNA. Available from: https://www.ncbi.nlm.nih.gov/books/NBK26837/ (Year: 2002).*
Han et al. "RecJ exonuclease: substrates, products and interaction with SSB." Nucleic Acids Research 34(4): 1084-1091 (2006).
Jensen et al. "RecJ 5' exonuclease digestion of oligonucleotide failure strands: a "green" method of trityl-on purification." Biochemistry 56(18): 2417-2424 (2017).
Lovett et al. "Identification and purification of a single-stranded-DNA-specific exonuclease encoded by the recJ gene of *Escherichia coli*." Proceedings of the National Academy of Sciences 86(8): 2627-2631 (1989).

* cited by examiner

*Primary Examiner* — Nancy J Leith
*Assistant Examiner* — Jessica D Parisi
(74) *Attorney, Agent, or Firm* — NIXON PEABODY LLP; Ronald I. Eisenstein; Jeanne N. Jodoin

(57) ABSTRACT

The present invention relates to methods of enriching target single-stranded nucleic acids in a mixed population of single-stranded nucleic acids. The method involves protecting the target single-stranded nucleic acids and using a 5' exonuclease to digest the non-target single-stranded nucleic acids. The invention also relates to methods of cloning target single-stranded nucleic acids into vectors, and to associated compositions and kits.

17 Claims, 3 Drawing Sheets
Specification includes a Sequence Listing.

SEQUENCE LISTING

<160> NUMBER OF SEQ ID NOS: 14

<210> SEQ ID NO 1
<211> LENGTH: 85
<212> TYPE: DNA
<213> ORGANISM: Artificial Sequence
<220> FEATURE:
<223> OTHER INFORMATION: trial single-stranded (ss) DNA oligo library
<220> FEATURE:
<221> NAME/KEY: misc_feature
<222> LOCATION: (38)..(62)
<223> OTHER INFORMATION: ns indicate random nucleotides representing a
      random library

<400> SEQUENCE: 1
tcgaggccac catgggatat caagatcttg acgcatcnnn nnnnnnnnn nnnnnnnnn      60 nnatcgaatt caccccgggt gaagc                                          85

<210> SEQ ID NO 2
<211> LENGTH: 21
<212> TYPE: DNA
<213> ORGANISM: Artificial Sequence
<220> FEATURE:
<223> OTHER INFORMATION: Blocking oligo

<400> SEQUENCE: 2
gatatcccat ggtggcctcg a                                              21

<210> SEQ ID NO 3
<211> LENGTH: 21
<212> TYPE: RNA
<213> ORGANISM: Artificial Sequence
<220> FEATURE:
<223> OTHER INFORMATION: Blocking oligo

<400> SEQUENCE: 3
gauaucccau gguggccucg a                                              21

<210> SEQ ID NO 4
<211> LENGTH: 20
<212> TYPE: DNA
<213> ORGANISM: Artificial Sequence
<220> FEATURE:
<223> OTHER INFORMATION: 5' end of general sequence layout of the
      finished library

<400> SEQUENCE: 4
tggcctaact ggccggtacc                                                20

<210> SEQ ID NO 5
<211> LENGTH: 20
<212> TYPE: DNA
<213> ORGANISM: Artificial Sequence
<220> FEATURE:
<223> OTHER INFORMATION: 3' end of general sequence layout of the
      finished library

<400> SEQUENCE: 5
tcgacagatc tgaattccta                                              20

<210> SEQ ID NO 6
<211> LENGTH: 20
<212> TYPE: DNA
<213> ORGANISM: Artificial Sequence
<220> FEATURE:
<223> OTHER INFORMATION: blocking oligo

<400> SEQUENCE: 6
ggtaccggcc agttaggcca                                              20

<210> SEQ ID NO 7
<211> LENGTH: 20
<212> TYPE: RNA
<213> ORGANISM: Artificial Sequence
<220> FEATURE:
<223> OTHER INFORMATION: blocking oligo

<400> SEQUENCE: 7
gguaccggcc aguuaggcca                                              20

<210> SEQ ID NO 8
<211> LENGTH: 20
<212> TYPE: DNA
<213> ORGANISM: Artificial Sequence
<220> FEATURE:
<223> OTHER INFORMATION: 3' DNA primer for primer extension

<400> SEQUENCE: 8
taggaattca gatctgtcga                                              20

<210> SEQ ID NO 9
<211> LENGTH: 109
<212> TYPE: DNA
<213> ORGANISM: Artificial Sequence
<220> FEATURE:
<223> OTHER INFORMATION: new trial oligo of 109 bases
<220> FEATURE:
<221> NAME/KEY: misc_feature
<222> LOCATION: (53)..(72)
<223> OTHER INFORMATION: ns indicate random nucleotides and represent a
      random library

<400> SEQUENCE: 9
tgcgttggac actatcaatc taagccgtcc aggacacgga tctggacagc gannnnnnnn    60
nnnnnnnnnn nntgagctct gggaggcgat cgacagatct gaattccta              109

<210> SEQ ID NO 10
<211> LENGTH: 20
<212> TYPE: RNA
<213> ORGANISM: Artificial Sequence
<220> FEATURE:
<223> OTHER INFORMATION: 5' RNA blocking oligo

<400> SEQUENCE: 10
gauugauagu guccaacgca                                              20

<210> SEQ ID NO 11
<211> LENGTH: 20
<212> TYPE: DNA
<213> ORGANISM: Artificial Sequence
<220> FEATURE:
<223> OTHER INFORMATION: 5' end of general sequence layout of the
      finished library

<400> SEQUENCE: 11
tgcgttggac actatcaatc                                                   20

<210> SEQ ID NO 12
<211> LENGTH: 2689
<212> TYPE: DNA
<213> ORGANISM: Artificial Sequence
<220> FEATURE:
<223> OTHER INFORMATION: pSYN_ssDNA1

<400> SEQUENCE: 12

```
tcgaggccac catgggatat caagatcttg acgcgtagga attcaccccg ggtgaagctg        60
gcgtaatcat ggtcatagct gtttcctgtg tgaaattgtt atccgctcac aattccacac       120
aacatacgag ccggaagcat aaagtgtaaa gcctggggtg cctaatgagt gagctaactc       180
acattaattg cgttgcgctc actgcccgct ttccagtcgg gaaacctgtc gtgccagctg       240
cattaatgaa tcggccaacg cgcgggagag gcggtttgcg tattgggcg ctcttccgct        300 tcctcgctca ctgactcgct gcgctcggtc gttcggctgc ggcgagcggt atcagctcac       360
tcaaaggcgg taatacggtt atccacagaa tcaggggata acgcaggaaa gaacatgtga       420
gcaaaaggcc agcaaaaggc caggaaccgt aaaaaggccg cgttgctggc gtttttccat       480
aggctccgcc cccctgacga gcatcacaaa aatcgacgct caagtcagag gtggcgaaac       540
ccgacaggac tataaagata ccaggcgttt ccccctggaa gctccctcgt gcgctctcct       600
gttccgaccc tgccgcttac cggatacctg tccgcctttc tcccttcggg aagcgtggcg       660
ctttctcata gctcacgctg taggtatctc agttcggtgt aggtcgttcg ctccaagctg       720
ggctgtgtgc acgaaccccc cgttcagccc gaccgctgcg ccttatccgg taactatcgt       780
cttgagtcca acccggtaag acacgactta tcgccactgg cagcagccac tggtaacagg       840
attagcagag cgaggtatgt aggcggtgct acagagttct tgaagtggtg cctaactac        900 ggctacacta gaagaacagt atttggtatc tgcgctctgc tgaagccagt taccttcgga       960
aaaagagttg gtagctcttg atccggcaaa caaaccaccg ctggtagcgg tggtttttt       1020 gtttgcaagc agcagattac gcgcagaaaa aaaggatctc aagaagatcc tttgatcttt      1080 tctacgggt ctgacgctca gtggaacgaa aactcacgtt aagggatttt ggtcatgaga       1140
ttatcaaaaa ggatcttcac ctagatcctt ttaaattaaa aatgaagttt taaatcaatc      1200
taaagtatat atgagtaaac ttggtctgac agttaccaat gcttaatcag tgaggcacct      1260
atctcagcga tctgtctatt tcgttcatcc atagttgcct gactccccgt cgtgtagata      1320
actacgatac gggagggctt accatctggc cccagtgctg caatgatacc gcgagaccca      1380
cgctcaccgg ctccagattt atcagcaata accagccag ccggaagggc cgagcgcaga       1440
agtggtcctg caactttatc cgcctccatc cagtctatta attgttgccg gaagctaga       1500 gtaagtagtt cgccagttaa tagtttgcgc aacgttgttg ccattgctac aggcatcgtg      1560
gtgtcacgct cgtcgtttgg tatggcttca ttcagctccg gttcccaacg atcaaggcga      1620
gttacatgat cccccatgtt gtgcaaaaaa gcggttagct ccttcggtcc tccgatcgtt      1680
gtcagaagta agttggccgc agtgttatca ctcatggtta tggcagcact gcataattct      1740
cttactgtca tgccatccgt aagatgcttt tctgtgactg gtgagtactc aaccaagtca      1800
ttctgagaat agtgtatgcg gcgaccgagt tgctcttgcc cggcgtcaat acgggataat      1860
accgcgccac atagcagaac tttaaaagtg ctcatcattg gaaaacgttc ttcggggcga      1920
```

| | |
|---|---|
| aaactctcaa ggatcttacc gctgttgaga tccagttcga tgtaacccac tcgtgcaccc | 1980 |
| aactgatctt cagcatcttt tactttcacc agcgtttctg ggtgagcaaa acaggaagg | 2040 |
| caaaatgccg caaaaaggg aataagggcg acacggaaat gttgaatact catactcttc | 2100 |
| ctttttcaat attattgaag catttatcag ggttattgtc tcatgagcgg atacatattt | 2160 |
| gaatgtattt agaaaaataa acaaataggg gttccgcgca catttccccg aaaagtgcca | 2220 |
| cctgacgtct aagaaaccat tattatcatg acattaacct ataaaaatag gcgtatcacg | 2280 |
| aggcccttc gtctcgcgcg tttcggtgat gacggtgaaa acctctgaca catgcagctc | 2340 |
| ccggagacgg tcacagcttg tctgtaagcg gatgccggga gcagacaagc ccgtcagggc | 2400 |
| gcgtcagcgg gtgttggcgg gtgtcggggc tggcttaact atgcggcatc agagcagatt | 2460 |
| gtactgagag tgcaccatat gcggtgtgaa ataccgcaca gatgcgtaag gagaaaatac | 2520 |
| cgcatcaggc gccattcgcc attcaggctg cgcaactgtt gggaagggcg atcggtgcgg | 2580 |
| gcctcttcgc tattacgcca gctggcgaaa gggggatgtg ctgcaaggcg attaagttgg | 2640 |
| gtaacgccag ggttttccca gtcacgacgt tgtaaaacga cggccagtg | 2689 |

<210> SEQ ID NO 13
<211> LENGTH: 2761
<212> TYPE: DNA
<213> ORGANISM: Artificial Sequence
<220> FEATURE:
<223> OTHER INFORMATION: pSYN_ssDNA2

<400> SEQUENCE: 13

| | |
|---|---|
| cctaaattgt aagcgttaat attttgttaa aattcgcgtt aaattttgt taaatcagct | 60 |
| cattttttaa ccaataggcc gaaatcggca aaatccctta taaatcaaaa gaatagaccg | 120 |
| agatagggtt gagtggccgc tacagggcgc tcccattcgc cattcaggct gcgcaactgt | 180 |
| tgggaagggc gtttcggtgc gggcctcttc gctattacgc cagctggcga aggggatg | 240 |
| tgctgcaagg cgattaagtt gggtaacgcc agggttttcc cagtcacgac gttgtaaaac | 300 |
| gacggccagt gagcgcgacg taatacgact cactataggg cgaattggcg aaggccgtc | 360 |
| aaggccacg tgtcttgtcca gagctcgcat aataaaatat cttattttc attacatctg | 420 |
| tgtgttggtt ttttgtgtgg cggccgcgtg gcctaactgg ccggtacctc gaggcgccgg | 480 |
| cgactagtcg acagatctga attcctagag tcggggcggc cggccgcttc gagcagacat | 540 |
| gataagatac attgatgagt ttggacaaac cacaactaga atgcagtgaa aaaaatgctt | 600 |
| tatttgtgaa atttgtgatg ctattgcttt atttgtaacc attataagct gcaataaaca | 660 |
| agttaacaac aacaattgca ttcatttat gtttcaggtt caggggggagg tgtgggaggt | 720 |
| ttttaaagc aagtaaaacc tctacaaatg tggtaaaatc gataaggatc cgtggtacct | 780 |
| ggagcacaag actggcctca tgggccttcc gctcactgcc cgctttccag tcgggaaacc | 840 |
| tgtcgtgcca gctgcattaa catggtcata gctgtttcct tgcgtattgg gcgctctccg | 900 |
| cttcctcgct cactgactcg ctgcgctcgg tcgttcgggt aaagcctggg gtgcctaatg | 960 |
| agcaaaaggc cagcaaaagg ccaggaaccg taaaaaggcc gcgttgctgg cgttttccca | 1020 |
| taggctccgc ccccctgacg agcatcacaa aaatcgacgc tcaagtcaga ggtggcgaaa | 1080 |
| cccgacagga ctataaagat accaggcgtt tcccctgga agctccctcg tgcgctctcc | 1140 |
| tgttccgacc ctgccgctta ccggatacct gtccgccttt ctcccttcgg gaagcgtggc | 1200 |
| gctttctcat agctcacgct gtaggtatct cagttcggtg taggtcgttc gctccaagct | 1260 |
| gggctgtgtg cacgaacccc ccgttcagcc cgaccgctgc gccttatccg gtaactatcg | 1320 |

```
tcttgagtcc aacccggtaa gacacgactt atcgccactg gcagcagcca ctggtaacag    1380
gattagcaga gcgaggtatg taggcggtgc tacagagttc ttgaagtggt ggcctaacta    1440
cggctacact agaagaacag tatttggtat ctgcgctctg ctgaagccag ttaccttcgg    1500
aaaaagagtt ggtagctctt gatccggcaa acaaaccacc gctggtagcg gtggttttt    1560 tgtttgcaag cagcagatta cgcgcagaaa aaaggatct caagaagatc ctttgatctt    1620
ttctacgggg tctgacgctc agtggaacga aaactcacgt taagggattt tggtcatgag    1680
attatcaaaa aggatcttca cctagatcct tttaaattaa aaatgaagtt ttaaatcaat    1740
ctaaagtata tatgagtaaa cttggtctga cagttaccaa tgcttaatca gtgaggcacc    1800
tatctcagcg atctgtctat ttcgttcatc catagttgcc tgactccccg tcgtgtagat    1860
aactacgata cgggagggct taccatctgg ccccagtgct gcaatgatac cgcgagaacc    1920
acgctcaccg gctccagatt tatcagcaat aaaccagcca gccggaaggg ccgagcgcag    1980
aagtggtcct gcaactttat ccgcctccat ccagtctatt aattgttgcc gggaagctag    2040
agtaagtagt tcgccagtta atagtttgcg caacgttgtt gccattgcta caggcatcgt    2100
ggtgtcacgc tcgtcgtttg gtatggcttc attcagctcc ggttcccaac gatcaaggcg    2160
agttacatga tcccccatgt tgtgcaaaaa agcggttagc tccttcggtc ctccgatcgt    2220
tgtcagaagt aagttggccg cagtgttatc actcatggtt atggcagcac tgcataattc    2280
tcttactgtc atgccatccg taagatgctt ttctgtgact ggtgagtact caaccaagtc    2340
attctgagaa tagtgtatgc ggcgaccgag ttgctcttgc ccggcgtcaa tacgggataa    2400
taccgcgcca catagcagaa ctttaaaagt gctcatcatt ggaaaacgtt cttcggggcg    2460
aaaactctca aggatcttac cgctgttgag atccagttcg atgtaaccca ctcgtgcacc    2520
caactgatct tcagcatctt ttactttcac cagcgtttct gggtgagcaa aaacaggaag    2580
gcaaaatgcc gcaaaaaagg gaataagggc gacacggaaa tgttgaatac tcatactctt    2640
cctttttcaa tattattgaa gcatttatca gggttattgt ctcatgagcg gatacatatt    2700
tgaatgtatt tagaaaaata aacaatagg ggttccgcgc acatttcccc gaaaagtgcc    2760
a                                                                    2761
```

<210> SEQ ID NO 14
<211> LENGTH: 2760
<212> TYPE: DNA
<213> ORGANISM: Artificial Sequence
<220> FEATURE:
<223> OTHER INFORMATION: pSYN_ssDNA3

<400> SEQUENCE: 14

```
cctaaattgt aagcgttaat attttgttaa aattcgcgtt aaattttgt taaatcagct      60 cattttttaa ccaataggcc gaaatcggca aaatccctta taaatcaaaa gaatagaccg     120
agatagggtt gagtggccgc tacagggcgc tcccattcgc cattcaggct gcgcaactgt     180
tgggaagggc gtttcggtgc gggcctcttc gctattacgc cagctggcga aggggggatg     240
tgctgcaagg cgattaagtt gggtaacgcc agggttttcc cagtcacgac gttgtaaaac     300
gacggccagt gagcgcgacg taatacgact cactataggg cgaattggcg aaggccgtc     360 aaggccacgt gtcttgtcca gagctcgcat aataaaatat cttatttttc attacatctg     420
tgtgttggtt ttttgtgtgg cggccgcgtg cgttggacac tatcaatctc gagcgccggc     480
gactagtcga cagatctgaa ttcctagagt cggggcggcc ggccgcttcg agcagacatg     540
```

```
ataagataca ttgatgagtt tggacaaacc acaactagaa tgcagtgaaa aaaatgcttt      600
atttgtgaaa tttgtgatgc tattgcttta tttgtaacca ttataagctg caataaacaa      660
gttaacaaca acaattgcat tcattttatg tttcaggttc aggggaggt gtgggaggtt       720 ttttaaagca agtaaaacct ctacaaatgt ggtaaaatcg ataaggatcc gtggtacctg      780
gagcacaaga ctggcctcat gggccttccg ctcactgccc gctttccagt cgggaaacct     840
gtcgtgccag ctgcattaac atggtcatag ctgtttcctt gcgtattggg cgctctccgc     900
ttcctcgctc actgactcgc tgcgctcggt cgttcgggta agcctgggg tgcctaatga      960 gcaaaaggcc agcaaaaggc caggaaccgt aaaaaggccg cgttgctggc gttttttccat    1020 aggctccgcc cccctgacga gcatcacaaa aatcgacgct caagtcagag gtggcgaaac     1080
ccgacaggac tataaagata ccaggcgttt ccccctggaa gctccctcgt gcgctctcct     1140
gttccgaccc tgccgcttac cggatacctg tccgcctttc tcccttcggg aagcgtggcg     1200
ctttctcata gctcacgctg taggtatctc agttcggtgt aggtcgttcg ctccaagctg     1260
ggctgtgtgc acgaaccccc cgttcagccc gaccgctgcg ccttatccgg taactatcgt     1320
cttgagtcca acccggtaag acacgactta tcgccactgg cagcagccac tggtaacagg     1380
attagcagag cgaggtatgt aggcggtgct acagagttct tgaagtggtg cctaactac      1440 ggctacacta gaagaacagt attggtatc tgcgctctgc tgaagccagt taccttcgga      1500
aaaagagttg gtagctcttg atccggcaaa caaaccaccg ctggtagcgg tggttttttt     1560
gtttgcaagc agcagattac gcgcagaaaa aaaggatctc aagaagatcc tttgatcttt     1620
tctacggggt ctgacgctca gtggaacgaa aactcacgtt aagggatttt ggtcatgaga     1680
ttatcaaaaa ggatcttcac ctagatcctt ttaaattaaa aatgaagttt taaatcaatc     1740
taaagtatat atgagtaaac ttggtctgac agttaccaat gcttaatcag tgaggcacct     1800
atctcagcga tctgtctatt tcgttcatcc atagttgcct gactccccgt cgtgtagata     1860
actacgatac gggagggctt accatctggc cccagtgctg caatgatacc gcgagaacca     1920
cgctcaccgg ctccagattt atcagcaata aaccagccag ccggaagggc cgagcgcaga     1980
agtggtcctg caactttatc cgcctccatc cagtctatta attgttgccg ggaagctaga     2040
gtaagtagtt cgccagttaa tagtttgcgc aacgttgttg ccattgctac aggcatcgtg     2100
gtgtcacgct cgtcgtttgg tatggcttca ttcagctccg gttcccaacg atcaaggcga     2160
gttacatgat cccccatgtt gtgcaaaaaa gcggttagct ccttcggtcc tccgatcgtt     2220
gtcagaagta agttggccgc agtgttatca ctcatggtta tggcagcact gcataattct     2280
cttactgtca tgccatccgt aagatgcttt tctgtgactg gtgagtactc aaccaagtca     2340
ttctgagaat agtgtatgcg gcgaccgagt tgctcttgcc cggcgtcaat acgggataat     2400
accgcgccac atagcagaac tttaaaagtg ctcatcattg gaaaacgttc ttcggggcga     2460
aaactctcaa ggatcttacc gctgttgaga tccagttcga tgtaacccac tcgtgcaccc     2520
aactgatctt cagcatcttt tactttcacc agcgtttctg ggtgagcaaa aacaggaagg     2580
caaaatgccg caaaaaaggg aataagggcg acacggaaat gttgaatact catactcttc     2640 cttttcaat attattgaag catttatcag ggttattgtc tcatgagcgg atacatattt      2700
gaatgtattt agaaaaataa acaaataggg gttccgcgca catttccccg aaaagtgcca     2760
```

METHODS AND COMPOSITIONS FOR ENRICHING NUCLEIC ACIDS

CROSS-REFERENCE TO RELATED APPLICATIONS

This application is a 35 U.S.C. § 371 National Phase Entry Application of International Application No. PCT/GB2019/050500 filed Feb. 25, 2019, which claims priority to GB Provisional Application No. 1803240.9 filed Feb. 28, 2018, the contents of each of which are incorporated in their entirety by reference herein.

SEQUENCE LISTING

The instant application contains a Sequence Listing that has been submitted in ASCII format via EFS-Web and is hereby incorporated by reference in its entirety. Said ASCII copy, created on Feb. 25, 2019, is named "Sequence listing_652120.txt" and is 13,997 bytes in size.

The present invention relates to methods, compositions and kits for enriching or purifying populations of nucleic acids, particularly, populations of single-stranded oligonucleotides. The invention finds particularly utility in enriching or purifying populations of single-stranded nucleic acids produced through artificial nucleic acid synthesis, and especially those produced through artificial DNA oligonucleotide synthesis. The present invention also relates to methods of cloning enriched nucleic acids into vectors.

BACKGROUND OF THE INVENTION

Methods of chemically synthesising nucleic acids, and in particular de novo synthesis of oligonucleotides, are important enabling technologies in molecular biology. Various methods of synthesising nucleic acids are known in the art.

The phosphoramidite method of oligonucleotide synthesis has been pivotal for the development of synthetic oligonucleotides. This process synthesises oligonucleotides in the 3' to 5' direction, with the 3' terminal nucleotide fixed to a solid support. The nucleotide to be coupled is added to the mixture with a phosphoramidite group to facilitate coupling to the 5' hydroxyl of the fixed nucleotide, and a dimethoxytrityl (DMT) group at the 5' position of the added nucleotide acting as a protecting group against self-polymerisation. The phosphoramidite group is oxidised to a phosphate, and acetic anhydride is then added to cap any uncoupled 5' hydroxyl groups of the fixed 3' nucleotide with an acetyl. This step is necessary in order to prevent internal deletions to the synthetic sequence caused by incomplete coupling. The DMT is then removed from the 5' hydroxyl of the newly-coupled 5' terminal nucleotide and the cycle begins again with the next nucleotide in the sequence. When all of the coupling steps to generate the target oligonucleotide have been carried out, the oligonucleotides are cleaved from the solid support and the phosphoramidite and DMT groups are removed. As the coupling steps of this method are not 100% efficient, this results in lower yield of full length product (FLP) as the length of the synthetic oligonucleotide, and therefore the number of coupling reactions, increases. This results in an accumulation of shorter acetyl-capped, truncated oligonucleotides as a by-product due to premature termination of the oligonucleotide synthesis.

Oligonucleotide synthesis can be particularly beneficial for the generation of libraries of synthetic oligonucleotides. For example, such libraries can comprise a host of transcription regulation sequences (e.g. combinations of transcription factor binding sites or enhancers) to be tested in a massively parallel reporter assay (MPRA). MPRAs involve generation of large libraries of vectors containing a reporter gene under control of many different translation regulation sequences. The translation regulation sequences each consist of a different combination of transcription factor binding sites (TFBS), enhancer sequences and/or other transcription regulating elements. Such assays are used to identify synthetic promoter sequences that can provide desired transcription of the reporter gene (e.g. at a desired level, or in a condition specific manner). These synthetic oligonucleotides may contain nucleic acid tags (sometimes known as barcode sequences) in order to easily identify the specific translation regulation sequences that result in the most effective transcription of the reporter gene. In order to correctly identify the synthetic enhancer, it is vital that the synthetic oligonucleotide library is of high quality, and that the correspondence between nucleic acid tags and translation regulation sequences is maintained. Other libraries can of course be produced by oligonucleotide synthesis, e.g. libraries of sequences coding for multiple variants of proteins.

However, using current oligo synthesis techniques, only approximately 13% of synthesized single-stranded DNA oligonucleotides that are 200 bases in length will be FLP, and thus contain the entire intended sequence from the 5' to the 3' end. The majority of oligonucleotides (~87%) will be truncated and lack the intended 5' end of the sequence. These truncated oligonucleotides interfere with downstream molecular biology methods, such as cloning.

Known methods of purifying the FLP from a synthetic oligonucleotide mixture include PCR amplification to increase yield of the FLP, trityl-on purification (TOP) and PAGE (Polyacrylamide Gel Electrophoresis).

PAGE purification can be effective at removing truncated oligonucleotides, but results in low yields due to inevitable losses during the electrophoresis process. This is particularly problematic for libraries where each member of library is typically present in very small quantities, which is typically the case for libraries of synthetic transcription regulation sequences discussed above.

As an alternative to PAGE, manufacturers recommend PCR to amplify full-length oligonucleotides and thereby increase the concentration of the FLP. However, when used for the amplification of oligonucleotide libraries, especially those with repetitive sequences and/or that share regions of sequence identity (such as libraries of synthetic transcription regulation sequences), template switching can occur. This results in chimeric products. Where nucleic acid tags are used, it also results in the loss of the vital correspondence between a given barcode and the intended transcription regulation sequence, which yields misleading results.

TOP utilises the DMT protecting group to purify the FLP from oligonucleotide synthesis. In this method, the DMT group is not removed from the oligonucleotide before cleavage from the solid support, allowing the FLP to be effectively purified using solid phase extraction tubes containing a hydrophobic resin. The hydrophobic DMT group is retained for longer on the hydrophobic resin than the unprotected shorter oligonucleotides, allowing the FLP to be washed from the resin after the prematurely terminated oligonucleotides have been eluted. However, the cleavage of the DMT from the purified oligonucleotide is carried out under harsh acidic conditions and can result in depurination of the target oligonucleotide, reducing the yield and purity of the FLP.

Single-stranded oligonucleotides can be enzymatically digested by exonucleases. Single-stranded exonucleases which operate from 5' to 3' are known in the art, and have previously been used in conjunction with a protecting group coupled to the terminal 5' oligonucleotide to protect the FLP from digestion while removing the unprotected prematurely terminated by-products from the reaction mixture. 5' protecting groups that have been used to inhibit degradation by 5' exonucleases include DMT (Jensen, M. & Davis, R. RecJ 5' Exonuclease Digestion of Oligonucleotide Failure Strands: A "Green" Method of Trityl-On Purification. Biochemistry, 56, 2417-2424 (2017)) and phosphorothioate (U.S. Pat. No. 8,728,767). However, as with TOP this method still requires the removal of the 5' protecting group after purification under conditions which may damage the FLP. This method also requires strict storage conditions to prevent degradation of the protecting group from the FLP, which would result in this prematurely deprotected product being digested by the exonuclease and reduce the final yield of FLP.

There is a need for alternative and improved methods of enriching mixed populations of nucleic acids, particularly mixed populations of single-stranded nucleic acids resulting from oligonucleotide synthesis, for desired sequences. In particular, there is a need for improved methods of enriching libraries produced by oligonucleotide synthesis for the desired full-length product, where conventional approaches such as PAGE and PCR are problematic.

STATEMENTS OF THE INVENTION

In a first aspect, the present invention provides a method for enriching target single-stranded nucleic acids in a mixed population of single-stranded nucleic acids, said method comprising:
a) providing a mixed population of single-stranded nucleic acids containing target single-stranded nucleic acids and non-target single-stranded nucleic acids, wherein the target single-stranded nucleic acids comprise a target sequence at or near their 5' ends;
b) contacting the mixed population of single-stranded nucleic acids with a blocking oligonucleotide, wherein the blocking oligonucleotide is capable of hybridising to the target sequence of the target single-stranded nucleic acids;
c) contacting the mixed population of nucleic acids of step b) with a single-strand specific 5' exonuclease; and
d) incubating the mixed population of nucleic acids of step c) under suitable conditions for the 5' exonuclease to digest the non-target single-stranded nucleic acids, such that the target single-stranded nucleic acids are enriched.

In this method, binding of the blocking oligonucleotide to the target sequence in the target single-stranded nucleic acids creates a double-stranded duplex at or near the 5' end of the target nucleic acids, which protects the target single-stranded nucleic acids from digestion by the single-strand specific 5' exonuclease. The non-target single-stranded nucleic acids are not protected by the formation of a duplex with the blocking oligonucleotide at or near the 5' end, and are therefore digested by the single-strand specific 5' exonuclease.

It is generally preferred that the single-stranded nucleic acids are DNA. However, in some embodiments the single-stranded nucleic acids can be RNA.

In a preferred embodiment of the invention, the mixed population of single-stranded nucleic acids is a population of single-stranded synthesised oligonucleotides. Suitably the mixed population of single-stranded oligonucleotides is the product of solid-phase oligonucleotide synthesis. Preferably the non-target single-stranded oligonucleotides (which may be referred to as "non-target oligonucleotides" or "non-target oligos" for brevity) are those that are formed by premature termination of oligo synthesis, e.g. due to coupling inefficiency (referred to as "truncated oligonucleotides" or "truncated oligos"). Oligonucleotide synthesis is typically carried out in the 3' to 5' direction, and thus it will be apparent that truncated oligonucleotides will be truncated at their 5' ends, which results in the lack of a target sequence. It will be understood that some truncated oligonucleotides may be nearly full-length, and thus may comprise at least part of the target sequence; whether such oligonucleotides are enriched in the method will depend on whether the blocking oligonucleotides is able to bind to the target sequence under the incubation conditions in step d) strongly enough to prevent the single-strand specific 5' exonuclease from digesting them. Those that are adequately protected can be considered target single-stranded nucleic acids as they are of satisfactory length.

In one preferred embodiment of the invention, the mixed population of single-stranded nucleic acids comprises a library of nucleic acids. The library may comprise members that have repetitive sequences and/or members that share significant regions of sequence identity. For example, the mixed population of single-stranded nucleic acids can comprise a library (e.g. a combinatorial library) that is generated from various combinations of a plurality of sequence elements. The library can suitably comprise a library of synthetic transcription regulation sequences generated from a plurality of regulatory sequence elements, as discussed in the introduction above. A library of synthetic transcription regulation sequences can be generated by combining various individual regulatory elements (e.g. transcription factor binding sites, enhancer sequences, etc.) in different possible combinations. Such libraries are known in the art. In some embodiments, each unique member of the library is linked to a corresponding identifying nucleic acid tag (e.g. a so-called barcode sequence), which is useful in reporter assays.

One of the challenges in using such libraries is that the use of PCR to amplify and/or purify the library typically results in a significant amount of template switching as a result of repetitive sequences and/or sequence similarity between the various library members. This results in the generation of unintended new chimeric sequences that were not in the original library. In the situation where individual library members are linked to a corresponding nucleic acid tag, this can result in a loss of the correspondence of a given tag to a particular library member. This is disastrous because the ability to generate reliable expression data from each individual member of the library in an assay is lost. Accordingly, it is typically not possible to use PCR to amplify such libraries. Furthermore, PAGE is typically not appropriate, especially given that such libraries are typically generated in very low quantities, with low copy numbers of each library member. This provides a significant challenge in terms of cloning of the library. Accordingly, the presence of truncated oligos is particularly problematic in synthetic libraries of comparatively long oligonucleotides (e.g. 80-100 bases or longer), as truncated sequences are present in relatively large quantities with respect to the full-length nucleic acids. Without the ability to amplify the desired sequences via PCR, and thereby "dilute out" the truncated oligos and their deleterious effects, this has major negative impacts on the ability to successfully clone and use such libraries. The present invention provides a tool to remove truncated oligonucleotides from such libraries, and thereby enrich the full length nucleic acids, without the negative effects of PCR, PAGE or other known approaches. It allows enrichment to be done in a manner that minimises losses of the desired full-length oligonucleotides, and also avoids issues with template switching.

The method of the present invention is not restricted to any particular length of target single-stranded nucleic acid. However, it is viewed as being of particular value in purifying the nucleic acid products of synthetic oligonucleotide synthesis. The method is viewed of being of particular value where the synthetic oligonucleotides are of a length where truncated oligos become a significant population of the nucleic acids produced, e.g. 10% or more, 25% or more, 50% or more, 75% or more, and optionally 85% or more. It will be appreciated that longer synthesised oligos will typically have a higher proportion of truncated oligo products than shorter synthesised oligos. The target single-stranded nucleic acids of the present invention are suitably from 50 to 1000 nucleotides in length, preferably from 100 to 1000 nucleotides in length, more preferably from 150 to 750 in nucleotides in length.

It will be apparent that non-target single-stranded nucleic acids typically do not comprise a target sequence at or near their 5' ends. They may, in some cases, comprise a partial target sequence, but in non-target single-stranded nucleic acids the target sequence will be non-functional, i.e. the blocking oligo will be unable to bind, or will bind only weakly, under the incubation conditions used in step d).

The Tm value of the blocking oligo can be any value that allows for suitable hybridisation of the blocking oligo to the target sequence in order to block the single-strand specific 5' exonuclease, and preferably to permit subsequent denaturation of the blocking oligo and the target sequence for downstream processes. It is typically preferred that the blocking oligo has a melting temperature (Tm) of at least 45° C., preferably 47° C., and more preferably at least 49° C. In many cases a Tm of approximately 50° C. is considered optimal. References to Tm for the blocking oligo relate to the Tm when it is hybridised to the target sequence, which will typically be a perfectly complementary sequence (though in some cases it might not be). In general, the Tm of the blocking oligo should be higher than the incubation temperature used in step d), preferably at least 5° C. higher, more preferably at least 8° C. higher, more preferably at least 10° C. higher, and more preferably at least 12° C. higher. It will be appreciated that the Tm of the blocking oligo should be sufficient that hybridisation of the blocking oligo to the target sequence in step d) is thermodynamically highly favoured.

The Tm of a nucleic acid is a well-known property, defined as the temperature at which half of the DNA strands are in the random coil or single-stranded (ssDNA) state. Tm depends on the length of the DNA molecule and its specific nucleotide sequence. DNA, when in a state where its two strands are dissociated (i.e., the dsDNA molecule exists as two independent strands), is referred to as having been denatured by the high temperature. Tm values can be determined readily though conventional techniques, and can also be predicted using conventional software tools known in the art (as discussed in the examples). Suitably Tm for any sequence in the present application is calculated using the nearest neighbour thermodynamic algorithm (SantaLucia & Hicks, 2004), assuming a Na+ concentration of 50 mM, and a concentration of 0.25 µM of each oligo.

In preferred embodiments of the invention, the blocking oligo and target sequence are perfectly complementary.

It is preferred that the blocking oligo specifically hybridises to the target sequence. It is therefore preferred that no sequence that is identical or highly similar to the target sequence (e.g. 80% identical, 90% identical, or 95% identical) is present at another location in the target or non-target single-stranded nucleic acids. The skilled person can readily determine a suitable target sequence to achieve this.

In embodiments of the invention, the target sequence is from 10 to 50 nucleotides in length, preferably from 15 to 30 nucleotides in length, and suitably from 15 to 25 nucleotides in length. In some specific examples of the present invention, the target sequence is 21 nucleotides in length.

Suitably the target sequence is the same length as the blocking oligonucleotide. However, the blocking oligonucleotide can be longer than the target sequence, provided the blocking oligonucleotide retains the ability to suitably hybridise to the target sequence. In other words, the blocking oligonucleotide can have one or more regions that are not adapted to hybridise to the target nucleic acid, provided that the one or more regions do not interfere with the intended purpose of hybridising to a target single-stranded nucleic acid and protecting it from digestion by the single-strand specific 5' exonuclease.

In embodiments of the present invention, the target sequence is located at the 5' end of target single-stranded nucleic acid. In other words, the 5' end of the target single-stranded nucleic acid is suitably the 5' end of the target sequence. In other embodiments of the invention the 5' end of the target sequence may be located near to the 5' end of the target single-stranded nucleic acid. It will be appreciated that, so long as the blocking oligonucleotide acts to prevent digestion of the target single-stranded nucleic acids by the single-strand specific 5' exonuclease, this is sufficient. It is generally preferred that the target sequence is located within 7 or fewer nucleotides of the 5' end of the target single-stranded nucleic acid, preferably 5 or fewer, more preferably 3 or fewer. However, in some cases it could be located further from the 5' end of the target single-stranded nucleic acid.

It should also be noted that in some embodiments, it may be acceptable if the position of the target sequence allows for a short 5' region of the target single-stranded nucleic acid to be digested by the single-strand specific 5' exonuclease, e.g. if the target single-stranded nucleic acid comprises excess or redundant sequence at its 5' end.

The blocking oligonucleotide may suitably be RNA or DNA. In some preferred embodiments of the invention the blocking oligonucleotide is RNA. In some particularly preferred embodiments of the invention the blocking oligonucleotide is RNA and the target and non-target single-stranded nucleic acids are not RNA (e.g. they are DNA). This provides an advantage in that the blocking oligonucleotide can be removed by digestion with a ribonuclease (RNase) leaving the target single-stranded nucleic acids unaffected, as discussed below.

The relative quantities of the mixed population of single-stranded nucleic acids and the blocking oligonucleotide will vary depending on the nature of the reaction. Optimal relative quantities can be determined experimentally. In some preferred embodiments, the mixed population of single-stranded nucleic acids and the blocking oligonucleotide are provided at a ratio of from 1:10 to 10:1, respectively (defined by their molar concentration), suitably from 1:5 to 5:1, suitably form 1:3 to 3:1, and suitably from 1:2 to 2:1, and optionally approximately 1:1. For example, an equimolar ratio of 1:1 has been found to be effective in the experiments discussed below.

In some embodiments of the invention, the method comprises a step of partially or completely eliminating the blocking oligonucleotide. Elimination of the blocking oligonucleotide is in many cases desirable as it prevents the blocking oligonucleotide from interfering with downstream molecular biology procedures, especially those that require hybridisation of the target sequence to another nucleic acid. Elimination of the blocking oligonucleotide can comprise physically removing the blocking oligonucleotide from the enriched nucleic acids, or can comprise breaking down the blocking oligonucleotide, e.g. by partially or completely digesting it using an RNase.

Elimination of the blocking oligonucleotide can be conveniently achieved in the case where the blocking oligonucleotide is RNA and the target nucleic acid is not RNA (e.g. it is DNA), by digesting the blocking oligonucleotide with a ribonuclease (RNase), and this is a preferred embodiment of the invention. It will be apparent that in the present context an RNase enzyme is one that is specific for RNA, and which does not digest DNA. Thus, the method of the invention suitably comprises the step of adding an RNase to the enriched population of nucleic acids arising from step d), and incubating the mixture under suitable conditions such that the blocking oligonucleotide is digested by the RNase. Suitable RNase enzymes for use in the invention are well-known in the art, and several suitable enzymes can be found in Enzyme class EC 3.1.27. For example, the RNase for use in step D can suitably be RNase H or RNase If (both available from New England BioLabs (NEB)). In some cases a mixture of more than one RNase may be preferable, e.g. a mixture of RNase H and RNase If is a particularly preferred embodiment.

Where the blocking oligonucleotide is a phosphorylated DNA oligo, a suitable exonuclease could potentially be used to eliminate it (e.g. lambda exonuclease). However, where the exonuclease can also digest the target single-stranded nucleic acid, this is generally not preferred. For example, lambda exonuclease also digests ssDNA, so is it not favoured where the target single-stranded nucleic acid is ssDNA.

Thus, in general, the blocking oligonucleotide is preferably eliminated by a nuclease that is able to preferentially digest the blocking oligonucleotide compared to the target single-stranded nucleic acid. More preferably the nuclease is able to effectively digest the blocking oligonucleotide but is substantially unable to digest the target single-stranded nucleic acid.

In other cases, the blocking oligonucleotide can be removed by other means, for example, the blocking oligonucleotide could comprise a tag that is not present on the target single-stranded nucleic acids which allows the blocking oligonucleotide to be removed using an agent that binds to the tag. The tag could be a nucleic acid sequence, or could be a non-nucleic acid moiety (e.g. protein or peptide, or other conventional tag used in affinity purification). Alternatively, in the situation when the target single-stranded nucleic acids are not in solution, e.g. because they are coupled to a solid substrate (e.g. to a silicon wafer, beads, etc.), the blocking oligonucleotide can be removed from the tethered target single-stranded nucleic acids by washing following denaturation of the blocking oligonucleotide and target sequence.

The single-strand specific 5' exonuclease can be essentially any suitable enzyme which is single-strand specific, and which has specific 5' exonuclease activity (i.e. substantially no 3' exonuclease activity or endonuclease activity). The single-strand specific 5' exonuclease should of course be capable of digesting the non-target single-stranded nucleic acids, but substantially incapable of digesting the blocked target single-stranded nucleic acids. Suitable enzymes are known in the art. In a preferred embodiment of the invention, the single-strand specific 5' exonuclease is an RecJ enzyme, preferably RecJf. RecJ enzyme is an $Mg^{2+}$-dependent single-stranded DNA (ssDNA) exonuclease that degrades its substrates in the 5' to 3' direction. RecJ has a strong specificity for ssDNA and no 3'-5' exonuclease activity. Double-stranded DNA (dsDNA) is neither a substrate nor a competitive inhibitor of ssDNA exonuclease activity of RecJ. RecJf is a recombinant fusion protein of RecJ and maltose binding protein (MBP). It has the same enzymatic properties as wild-type RecJ. Fusion to MBP enhances RecJf solubility. RecJf is available from NEB under catalogue number M0264S. Other derivatives of RecJ could of course be used. Where the target single-stranded nucleic acid is an RNA, a suitable single-strand specific 5' exoribonuclease can be used. Such enzymes are known in the art, for example the exonuclease marketed as Terminator™ 5'-Phosphate-Dependent exonuclease by Lucigen (catalogue no TER51020). The single-strand specific 5' exonuclease may be provided in the reaction solution in any suitable concentration, and optimum concentrations can be derived experimentally for any reaction. For example, RecJf has been used successfully at concentrations of 3U, 6U, 9U in the examples discussed below.

The length of time for which the single-strand specific 5' exonuclease is incubated with the mixed population of nucleic acids should be sufficient to permit the single-strand specific 5' exonuclease to digest a significant proportion of the non-target single-stranded nucleic acids. Suitably the incubation time is sufficient for the single-strand specific 5' exonuclease to digest at least 50%, preferably at least 70%, more preferably at least 80%, more preferably at least 90%, and yet more preferably at least 95% of the non-target single-stranded nucleic acids. A suitable incubation period can be determined experimentally for any single-strand specific 5' exonuclease and mixed population of nucleic acids. The incubation temperature can be any temperature at which the single-strand specific 5' exonuclease is active. For example, temperatures in the range of from 20 to 40° C. can be suitable for most enzymes, with a temperature of approximately 37° C. being optimal in some cases. By way of non-limiting example, an insulation period of 4 h at 37° C. has been found to be effective, especially for RecJf, but other incubation periods and temperatures are contemplated.

The method preferably comprises the step of inactivating and/or removing the single-strand specific 5' exonuclease after it step d) has been completed. Suitably the single-strand specific 5' exonuclease is inactivated by heat treatment at a suitable temperature to permanently denature the single-strand specific 5' exonuclease. In the case of RecJ and RecJf, for example, this can be achieved by incubation at 65° C. for 20 minutes. Accordingly, it is typically preferred that the single-strand specific 5' exonuclease is thermolabile (e.g. at 65° C.). In other embodiments, the single-strand specific 5' exonuclease could be removed, e.g. by affinity purification techniques; this may be desirable in circumstances where heat treatment was not possible, e.g. due to the presence of other desired thermolabile components.

In some preferred embodiments of the invention, the method comprises providing a single-stranded binding protein (SSBP). SSBP binds to single-stranded DNA and prevents annealing of single-stranded DNA into double-stranded DNA. It has surprisingly been found that provision of SSBP in the method of the present invention can result in improved enrichment of the single-stranded target nucleic acids, and in some cases also assists in subsequence cloning of the enriched nucleic acid proteins into a vector (e.g. a plasmid). Preferably the SSBP is added to the mixed population of nucleic acids prior to addition of the single-strand specific 5' exonuclease. Without wishing to be bound by theory, it is believed that the SSBP prevents or reduces the formation of secondary structures in the target and non-target single-stranded nucleic acids, which can in some cases prevent the single-strand specific 5' exonuclease from digesting the non-target nucleic acids.

The SSBP is not particularly limited in its biological origin, as long as it has an activity that is similar to that of the single-strand binding protein of E. coli. Examples of SSBP include, but are not limited to ET SSB (extreme thermostable single-stranded DNA binding protein), E coli SSB, RecA and its homolog RAD51 in human, Tth RecA, human replication protein hRPA, herpes simplex virus 1CP8 protein, yRPA, and vaccinia virus SSBP. In some preferred embodiments, the SSBP is thermostable enough to resist inactivation under the conditions used to inactivate the single-strand specific 5' exonuclease. The SSBP may be provided at any suitable concentration, e.g. without limitation from 1 nM to 10 UM, preferably in an amount of 1 nM to 1.0 µM, 1 nM to 500 nM, 50 nM to 500 nM.

It will be apparent that the method of the present invention relies on the non-target single-stranded nucleic acids being susceptible to digestion by the single-strand specific 5' exonuclease. Thus, the non-target single-stranded nucleic acids comprise no modification or feature that is capable of protecting the target oligonucleotide from digestion by the single-strand specific 5' exonuclease. In general, in the method of the present invention, whether a nucleic acid of the mixed population of nucleic acids is digested by the single-strand specific 5' exonuclease is determined predominantly or solely by whether or not the blocking oligo binds to a target sequence in the nucleic acid and forms a duplex at or near the 5' end of the nucleic acid.

In the situation where the mixed population of single-stranded nucleic acids is a population of synthesised oligonucleotides (e.g. the product of solid-phase oligonucleotide synthesis), it is generally preferred that the synthesised oligonucleotides have been deprotected such that the single-strand specific 5' exonuclease is able to digest the synthesised oligonucleotides under suitable conditions (in the absence of the blocking oligonucleotide). In particular, any 5' protecting groups are preferably removed (e.g. dimethoxytrityl) from the synthesised oligonucleotides, and more preferably the synthesised oligonucleotides are fully deprotected.

Accordingly, in some embodiments of the invention the method may suitably comprise a step of treating the mixed population of single-stranded nucleic acids to render them susceptible to digestion by the single-strand specific 5' exonuclease. It will be apparent that this step is preferably carried out prior to addition of the single-strand specific 5' exonuclease, and preferably it is carried out prior to addition of the blocking oligonucleotide.

In some embodiments of the present invention the mixed population of single-stranded nucleic acids is in solution. For example, a solution of synthesised oligonucleotides can be obtained by cleaving the link between the synthesised oligonucleotides and the substrate upon which they were synthesised. Where the mixed population of single-stranded nucleic acids is in solution, it is preferred that the blocking oligonucleotide is RNA and the target nucleic acid is not RNA (preferably it is DNA). In this case, the blocking oligonucleotide can be eliminated from the enriched target single-stranded nucleic acids through the use of a ribonuclease (RNase), as discussed above.

In other embodiments of the invention, the mixed population of single-stranded nucleic acids is attached to a substrate, i.e. some form of solid support. In such cases the nucleic acids are not in solution. In some non-limiting examples, the solid support can be a silicon wafer or a controlled pore glass (CPG) bead; these are substrates commonly used in oligonucleotide synthesis. When the single-stranded nucleic acids are not in solution, the blocking oligo, and indeed any other reagent, can be readily removed from the target single-stranded nucleic acids by washing.

The method suitably comprises the further steps of incorporating the target single-stranded nucleic acids into a vector, preferably a DNA vector, and most preferably a double-stranded DNA vector. Such a vector is suitably used for cloning of the target single-stranded nucleic acids.

The vector may be any suitable vector, including, but not limited to, plasmids, cosmids, viral vectors, gene therapy vectors, artificial chromosomes, or any other form of vector. In some preferred embodiments, the vector is a plasmid. The vector is suitably a cloning vector or an expression vector.

The method suitably comprises incubating the target single-stranded nucleic acids with the vector under suitable conditions for the target single-stranded nucleic acids to be incorporated into the vector.

Methods of incorporating nucleic acids into a vector are well-known in the art.

In some embodiments of the present invention, it is preferred that the target single-stranded nucleic acids are converted to double-stranded derivatives (i.e. target double-stranded nucleic acids) prior to incorporation into the vector. Conversion of the target single-stranded nucleic acids to target double-stranded nucleic acids can conveniently be achieved by:

contacting the target single-stranded nucleic acids with a primer which hybridises to the 3' end of the region to be converted to double-stranded form (typically at the 3' end of the target single-stranded nucleic acids);

providing a polymerase that extends the primer to produce the target double-stranded nucleic acids. For example, Phusion HF polymerase (New England Biolabs, Ipswich, MA, USA) and Klenow Fragment can be used to extend a 3' DNA primer hybridised to DNA target single-stranded nucleic acids. Other suitable polymerases will be apparent to the skilled person. The polymerase, primer and target single-stranded nucleic acids are incubated under suitable conditions for the second strand to be produced.

Conversion of the target single-stranded nucleic acids to target double-stranded nucleic acids is particular preferred when the target nucleic acids are to be incorporated into the vector using enzymatic assembly of overlapping DNA fragments (often referred to as Gibson Assembly®). Enzymatic assembly of overlapping DNA fragments assembly is extensively described in the literature—see for example Daniel G. Gibson, Methods in Enzymology, Volume 498, Chapter 15. WO2007/021944 and WO2016/033315 also describes various approaches to enzymatic assembly of overlapping DNA fragments.

Accordingly, in some preferred embodiments of the invention, the target single- or double-stranded nucleic acids and vector have corresponding overlapping regions configured to permit incorporation of the target single- or double-stranded nucleic acids in to the vector by enzymatic assembly of overlapping DNA fragments. Typically overlapping regions are provided at each end of the target single- or double-stranded nucleic acids, which correspond to overlapping regions provided at each end of a linear (e.g. linearised) double-stranded DNA vector.

Thus, in some embodiments of the invention, the method comprises treating a linear double-stranded DNA vector with an exonuclease that chews back the ends of the vector to produce a vector having single-stranded overhangs. The overhangs can be 3' or 5' overhangs, but are preferably 3' overhangs (3' overhangs are produced by a 5' exonuclease). When target double-stranded nucleic acids are to be incorporated into a vector having single-stranded overhangs, their ends are preferably also chewed back to provide corresponding single-stranded overhangs. This can be performed by the same exonuclease that chews back the linear double-stranded DNA vector or a different exonuclease, provided that nuclease creates the desired corresponding overhangs. Preferably it is performed by the same exonuclease, and yet more preferably the vector and target double-stranded nucleic acids are co-incubated with the exonuclease.

In some embodiments of the invention, the method comprises:
  i) providing a linear double-stranded DNA vector which comprises sequences at or near its 5' and 3' ends that overlap with sequences at the 5' and 3' ends of the target single- or double-stranded nucleic acids;
  ii) contacting the linear double-stranded DNA vector with an exonuclease, which chews back the ends of the double-stranded DNA vector to produce a vector having single-stranded overhangs;
  iii) contacting said vector having single-stranded overhangs with the target single-stranded nucleic acids or target double-stranded nucleic acids having single-stranded overhangs;
  iv) annealing complementary sequences of the target single- or double-stranded nucleic acids and the overhangs of vector to form an annealed vector product;
  v) contacting said annealed vector product with a DNA polymerase that extends the 3' ends to fill gaps in the annealed product; and
  vi) contacting the product of step v) with a ligase to heal nicks.

As discussed above, the single-stranded overhangs of the target double-stranded nucleic acids are suitably provided by contacting the target double-stranded nucleic acids with an exonuclease. Conveniently the single-stranded overhangs of the target double-stranded nucleic acids are provided by contacting the target double-stranded nucleic acids with the exonuclease together with the linear double-stranded DNA vector in step ii) of the method.

In preferred embodiments of the present invention, both the enrichment of target nucleic acids and incorporation of the target nucleic acids into the vector are performed in a single reaction vessel. This is advantageous as it minimises the losses due to transfer of the target nucleic acids.

In an aspect of the invention there is provided a method of cloning a nucleic acid, the method comprising:
  a) enriching target single-stranded nucleic acids (preferably DNA) in a mixed population of single-stranded nucleic acids, said enriching comprising:
    i) providing a mixed population of single-stranded nucleic acids containing target single-stranded nucleic acids and non-target single-stranded nucleic acids, wherein the target single-stranded nucleic acids comprise a target sequence at or near their 5' ends;
    ii) adding to the mixed population of single-stranded nucleic acids a blocking oligonucleotide, wherein the blocking oligonucleotide is capable of hybridising to the target sequence of the target single-stranded nucleic acids;
    iii) adding to the mixed population of nucleic acids of step ii) a single-strand specific 5' exonuclease;
    iv) incubating the mixed population of nucleic acids of step iii) under suitable conditions for the 5' exonuclease to digest the non-target single-stranded nucleic acids, such that the target single-stranded nucleic acids are enriched;
  b) incorporating the target single-stranded nucleic acids into a DNA vector, said incorporating comprising:
    i) optionally, converting of the target single-stranded nucleic acids to target double-stranded nucleic acids;
    ii) providing a linear double-stranded DNA vector which comprises sequences at or near its 5' and 3' ends that overlap with sequences at the 5' and 3' ends of the target single- or double-stranded nucleic acids;
    iii) contacting the linear double-stranded DNA vector with an exonuclease that chews back the ends of the double-stranded DNA vector to produce a vector having single-stranded overhangs;
    iv) where optional step i) is carried out, contacting the target double-stranded nucleic acids with an exonuclease that chews back the ends of the target double-stranded nucleic acids to produce overhangs corresponding to the single-stranded overhangs in the vector;
    v) contacting said vector having single-stranded overhangs with the target single-stranded nucleic acids or target double-stranded nucleic acids having single-stranded overhangs;
    vi) annealing complementary sequences of the target single- or double-stranded nucleic acids of step v) and the overhangs of vector to form an annealed product;
    vii) contacting said annealed product with a DNA polymerase that extends the 3' ends to fill gaps in the annealed product; and
    viii) contacting the annealed product with a ligase to heal nicks;
  thereby incorporating the enriched target single-stranded nucleic acids into the vector.

Preferably the method (i.e. both of steps a) and b)) are performed in a single reaction vessel.

It will be apparent that the target single-stranded nucleic acids are in double-stranded form once incorporated into the vector. In some embodiments single-stranded nucleic acids are in double-stranded form prior to incorporation into the vector, i.e. when optional step b) i) is carried out, and in other cases they are converted to double-stranded form in step b) vii).

The linear vector may suitably be a linearised circular vector, e.g. a linearised plasmid.

Preferably the exonuclease used in the methods of incorporating the target nucleic acids into the DNA vector is a double-stranded 5' exonuclease. The 5' exonuclease generates 3' single-stranded overhangs in the vector, and, if present, in the double-stranded derivatives of the target single-stranded nucleic acids. Suitable double-stranded 5' exonucleases for use in enzymatic assembly of overlapping DNA fragments are known in the art. T5 exonuclease is conventionally used, but T7 exonuclease or lambda exonuclease could also be used, for example.

It is preferred that the single-strand specific 5' exonuclease is removed or inactivated prior to contacting the vector with the target single- or double-stranded nucleic acids.

In preferred embodiments of the invention the target sequence of the target single- or double-stranded nucleic acids defines an overlapping sequence with the DNA vector into which the target single- or double-stranded nucleic acids are to be inserted.

In some embodiments of the invention it is preferred that SSBP is provided during incorporation of the target single- or double-stranded nucleic acids into the vector. As above, the SSBP is not particularly limited in its biological origin, as long as it has an activity that is similar to that of the single-strand binding protein of E. coli. Examples of SSBP include, but are not limited to ET SSB (extreme thermostable single-stranded DNA binding protein), E coli SSB, RecA and its homolog RAD51 in human, Tth RecA, human replication protein hRPA, herpes simplex virus 1CP8 protein, yRPA, and vaccinia virus SSBP. The SSB may be provided at any suitable concentration, e.g. without limitation from 1 nM to 10 µM, preferably in an amount of 1 nM to 1.0 µM, 1 nM to 500 nM, 50 nM to 500 nM.

It has been found that the present invention is suitable to allow successful cloning of nucleic acids comprising a high GC content. Accordingly, in some preferred embodiments of the invention, the target single- or double-stranded nucleic acids comprise a GC content of 55% or higher, suitably 60% or higher, and optionally 65% or higher.

In a further aspect, the present invention provides a composition or kit for the enrichment of target single-stranded nucleic acids in a mixed population of nucleic acids, wherein the target single-stranded nucleic acids comprise a target sequence at or near their 5' ends, said composition or kit comprising:
  a) a blocking oligonucleotide adapted to hybridise to the target sequence; and
  b) a single-strand specific 5' exonuclease.

Suitable and preferred blocking oligonucleotides and single-strand specific 5' exonucleases for the composition or kit are discussed above in respect of the methods.

The composition or kit suitably comprises a ribonuclease. Suitable and preferred ribonucleases for the composition or kit are discussed above.

The composition or kit suitably comprises a SSBP. Suitable and preferred SSBPs for the composition or kit are discussed above.

Other preferred or optional features of the above methods will be relevant to the composition or kit, as will be apparent to the skilled person.

In a further aspect, the present invention related to an enriched population of nucleic acids comprising target nucleic acids obtained or obtainable by the above methods.

In a further aspect, the present invention related to one or more vectors obtained or obtainable by the above methods.

It will be apparent to those of skill in the art upon reading this disclosure, each of the individual aspect or embodiments described herein has discrete components and features which can be readily separated from or combined with the features of any of the other embodiments or aspects. Any recited method can be carried out in the order of events recited or in any other order unless context or logic dictates otherwise.

Embodiments of the present invention will now be described, by way of non-limiting example, with reference to the accompanying drawings.

SPECIFIC DESCRIPTION OF EMBODIMENTS OF THE INVENTION

Figure 1:
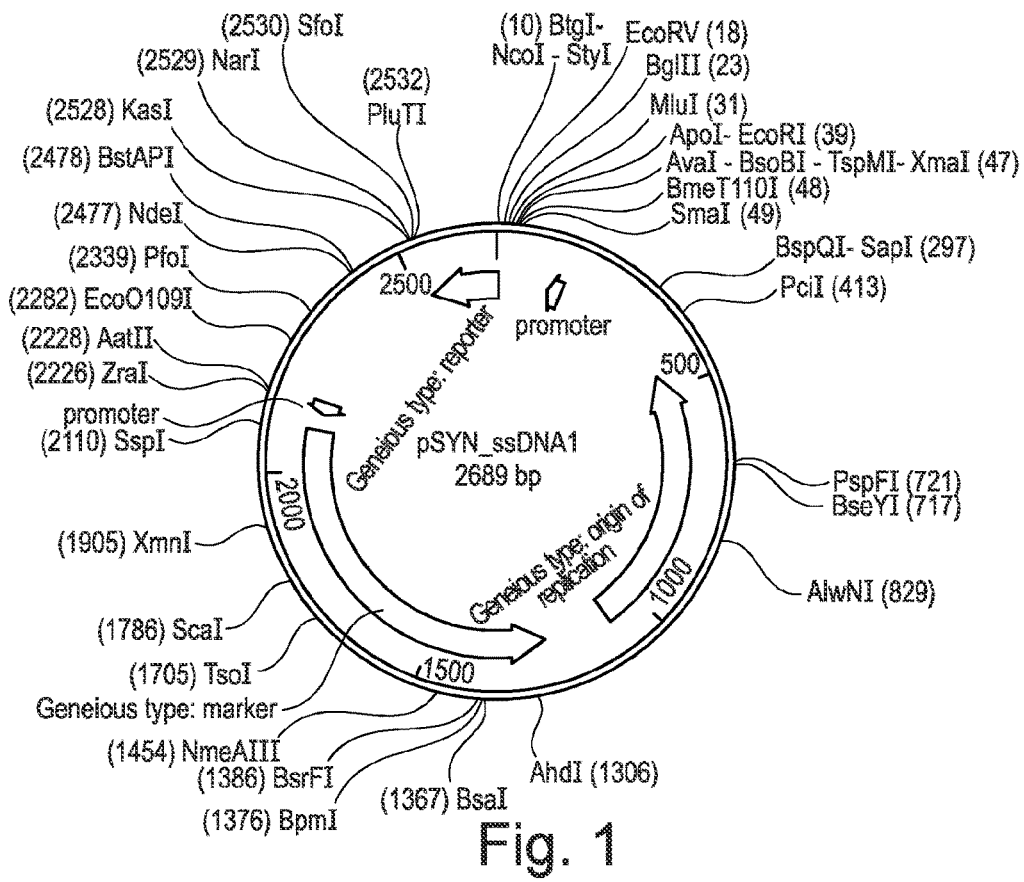
FIG. 1—plasmid map of pSYN_ssDNA1.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as Genome Analysis: A Laboratory Manual Series (Vols. I-IV), Using Antibodies: A Laboratory Manual, Cells: A Laboratory Manual, PCR Primer: A Laboratory Manual, and Molecular Cloning: A Laboratory Manual (all from Cold Spring Harbor Laboratory Press), Stryer, L. (1995) Biochemistry (4th Ed.) Freeman, New York, Gait, "Oligonucleotide Synthesis: A Practical Approach" 1984, IRL Press, London, Nelson and Cox (2000), Lehninger, Principles of Biochemistry $3^{rd}$ Ed., W.H. Freeman Pub., New York, N.Y. and Berg et al. (2002) Biochemistry, $5^{th}$ Ed., W.H. Freeman Pub., New York, N.Y., all of which are herein incorporated in their entirety by reference for all purposes.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

"Enrichment" or "enriching" in the present context refers to increasing the proportion of target single-stranded nucleic acids relative to non-target single-stranded nucleic acids. In the present invention this is achieved by digesting the non-target single-stranded nucleic acids using the exonuclease. While the nucleotides from which the non-target single-stranded nucleic acids were constructed remain in the mixture, the digested non-target single-stranded nucleic acids have ceased to exist in a meaningful sense. This can be viewed as synonymous with "purifying" the target single-stranded nucleic acids, and is also sometimes referred to in the art as "clean-up" of "cleaning-up" of the mixed population of single-stranded nucleic acids. Suitably the enrichment comprises at least a 2-fold increase in the proportion of target single-stranded nucleic acids to non-target single-stranded nucleic acids, preferably 4-fold, more preferably 10-fold, and more preferably 25-fold and suitably 100-fold. Suitably the proportion of non-target single-stranded nucleic acids is reduced by at least 50%, preferably at least 75%, more preferably at least 80%, preferably at least 90%, preferably at least 95%, and preferably at least 99%.

"Complementary" or "substantially complementary" refers to the hybridisation or base pairing between nucleotides or nucleic acids, such as, for instance, between the two strands of a double-stranded DNA molecule or between an oligonucleotide primer and a primer binding site on a single-stranded nucleic acid to be sequenced or amplified. Complementary nucleotides are, generally, A and T (or A and U), or C and G. Two single-stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, substantial complementary exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See, M. Kanehisa Nucleic Acids Res. 12:203 (1984), incorporated herein by reference.

The term "hybridisation" refers to the process in which two single-stranded polynucleotides bind non-covalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization."

"Hybridising specifically to" refers to the binding, duplexing, or hybridizing of a molecule substantially to, or only to, a particular nucleotide sequence or sequences under stringent conditions when that sequence is present in a complex mixture (e.g., total cellular DNA or RNA).

"Hybridisation probes" are oligonucleotides capable of binding in a base-specific manner to a complementary strand of nucleic acid. Such probes include peptide nucleic acids, as described in Nielsen et al., Science 254, 1497-1500 (1991), and other nucleic acid analogs and nucleic acid mimetics. See U.S. Pat. No. 6,156,501.

"Mixed population" refers to any sample containing both target (desired) and non-target (undesired) nucleic acids. As a non-limiting example, a mixed population of nucleic acids may be a population of synthesised oligonucleotides comprising a mixture of full-length oligonucleotides and shorter, truncated species resulting from incomplete synthesis. Moreover, a mixed population of nucleic acids may have been enriched for a given population but nonetheless includes other undesirable populations.

"Nucleic acids" according to the present invention may include any polymer or oligomer of pyrimidine and purine bases, preferably cytosine, thymine, and uracil, and adenine and guanine, respectively. See Albert L. Lehninger, PRINCIPLES OF BIOCHEMISTRY, at 793-800 (Worth Pub. 1982). The present invention contemplates in particular DNA and RNA, but peptide nucleic acids, and any chemical variants thereof, such as methylated, hydroxymethylated or glucosylated forms of these bases, are contemplated, as appropriate. The nucleic acids are preferably artificially or synthetically produced. The nucleic acids may be DNA or RNA, or a mixture thereof, and may exist permanently or transitionally in single-stranded or double-stranded form, including homoduplex, heteroduplex, and hybrid states. Nucleic acids may include modifications. Amino modifier reagents, for example, may be used to introduce a primary amino group into a nucleic acid.

An "oligonucleotide" is a nucleic acid ranging that is at least 5, preferably at least 10, and more preferably at least 20 nucleotides in length. Typically, an oligonucleotide will be at most 1000 nucleotides, preferably at most 500 nucleotides in length.

By "nucleic acid tag" is meant a short sequence of nucleotides (e.g., fewer than 40, 30, 25, 20, 15, 13, 12, 11, 10, 9, 8, 7, 6, 5, 4 or fewer nucleotides) included in a library member that is unique to that particular library member, and which is preferably present in an included in an mRNA transcript derived from that library member.

By "expression vector" is meant a nucleic acid that includes an open reading frame and, when introduced to a cell, contains all of the nucleic acid components necessary to allow mRNA expression of said open reading frame. "Expression vectors" of the invention also include elements necessary for replication and propagation of the vector in a host cell.

As used herein, the term "5' exonuclease" or "5'-3' exonuclease", refers to an exonuclease that degrades nucleic acid, especially DNA, from the 5' end, i.e., in the 5' to 3' direction.

"Single-strand specific 5' exonucleases" in the present context can remove nucleotides from the 5' end of a single-stranded nucleic acid molecule, especially DNA, but are substantively or completely unable to remove nucleotides from the 5' end of a double-stranded nucleic acid molecule.

Other "5' exonucleases" or "5'-3' exonucleases", are non-single-strand specific. Such non-single-strand specific 5' exonucleases, which are useful for cloning sequences into vectors, can remove nucleotides from the 5' end of a strand of double-stranded DNA at a blunt end and, in certain embodiments, at a 3' and or 5' overhang. T5 exonuclease, lambda exonuclease and T7 exonuclease are examples of non-single-strand specific 5'-3' exonucleases.

As used herein, the term "ligase", refers to an enzyme that can covalently join a 3' end of a DNA molecule to a 5' end of another DNA molecule, particularly at a nick. Examples of ligases include T7 ligase, T4 DNA ligase, *E. coli* DNA ligase and Taq ligase, although many others are known and may be used herein.

As used herein, the term "single-strand (ss) DNA binding protein" or "SSBP", refers to proteins that bind to single-stranded DNA and preferably prevent or remove secondary structure from the DNA to allow enzymes to function effectively upon it. Examples of ss DNA binding proteins are T4 gene 32 protein, *E. coli* SSB, T7 gp2.5 SSB, phage phi29 SSB, and ET SSB although many others, e.g., RedB of lambda phage, Reel of Rae prophage and the sequences listed below, are known and may be used herein. A thermostable SSBP that is stable at 50° C. may be used in some cases.

In the present application, the terms "oligonucleotide" and "oligonucleotides" may be abbreviated to "oligo" or "oligos", respectively.

As used herein, the term "overlapping sequence" or "overlap" or variants thereof, refers to a sequence that is complementary in two polynucleotides, and where the overlapping sequence is single-stranded on one polynucleotide it can be hybridized to another overlapping complementary single-stranded region on another polynucleotide. By way of example, the overlapping sequence may be complementary in at least 5, 10, 15, or more polynucleotides in a set of polynucleotides. An overlapping sequence may be at or close to (e.g., within about 5, 10, 20 nucleotides of) the ends of two distinct molecules (e.g., the 3' ends of two single-stranded oligonucleotides, or the 3' end of the top strand of first double-stranded polynucleotide and the 3' end of the bottom strand of a second ds molecule). An overlapping sequence may vary in length and, in some cases, may be at least 12 nucleotides in length (e.g. at least 15, 20 or more nucleotides in length). While there is no specific upper length for the overlapping sequence, in the present context the overlapping sequence will typically be less than 50 nucleotides in length (e.g., up to 30, up to 20 or up to 15 nucleotides in length). The minimum length of the overlap may be defined by a Tm that is preferably equal to or greater than 48° C.

As used herein a "vector" is a suitable nucleic acid, typically DNA, into which a target nucleic acid may be incorporated such that the vector containing the target nucleic acid can be replicated in a host cell. A linearized vector may be created restriction endonuclease digestion of a circular vector or by PCR.

The concentration of nucleic acids (e.g. target nucleic acids and/or linearized vectors) can be determined by gel electrophoresis or other known means.

"Thermostable" refers to a protein (e.g. enzyme) that retains at least 95% of its activity after 10 minutes at a temperature of 65° C. "Thermolabile" or "temperature sensitive" refers to a protein (e.g. enzyme) that loses at least 95% of its activity after 10 minutes at a temperature of 65° C.

EXAMPLES

Example 1—Clean Up and Cloning Long Single-Stranded Oligonucleotides into Double Stranded Plasmid Vectors

SUMMARY

Long oligonucleotides (oligos) synthesised without a purification step contain a significant quantity of short, incomplete fragments (truncated oligos). In many cases the truncated oligos significantly outnumber the full-length oligos. This is due to the cumulative effects of the imperfect coupling efficiency of the DNA synthesis reaction which is around 99% efficient. The incomplete fragments (truncated oligos) can interfere with downstream molecular biology applications, such as cloning. An oligo can be viewed as long in this context if it is more than about 100 nucleotides in length. Typically, the longer the oligo, the greater the proportion of truncated oligos.

An enzymatic enrichment (clean-up) method was optimised with a test library of medium-length oligos of 85 bases in length. The clean-up methods were then tested in a library of 18,000 different sequences over 190 bases in length.

The method will be invaluable to molecular biologists wishing to take advantage of the advances in DNA synthesis reactions, which are increasing the lengths of synthesised oligos. Moreover, the method it is of particular value where PCR cannot readily be used to amplify desired (target) nucleic acids (e.g. full-length oligos) to increase the amount of target single-stranded nucleic acids for downstream methods such as cloning, and to enrich the full-length (target) nucleic acids with respect to undesired (non-target) oligos (e.g. truncated oligos). As discussed above, this is particularly the case for libraries with repetitive sequences, and for libraries which have significant regions of sequence similarity across members.

Methods

Optimising the Enzymatic Clean-Up Method

An enzymatic clean-up method for long oligonucleotides (oligos) was optimised using an 85-base trial oligo library. An in-house destination vector, modified from a pUC19 vector (pSYN_ssDNA1—sequence below and map shown in FIG. 1), was selected and two restriction enzyme sites EcoRI and EcoRV were chosen to linearise the vector. The vector was digested with EcoRI-HF and EcoRV-HF (both New England Biolabs, Ipswich, MA, USA) as per manufacturer's protocol and cleaned up using AMPure XP beads following standard protocol (Agencourt®AMPure® XP, Agilent, Santa Clara, CA, USA).

The trial single-stranded (ss) DNA oligo library was designed with a 20 to 21 base sequence flanking the 5' and 3' ends identical to the first 21/20 bases of sequence counting from each end of the linearised vector and with a calculated melting temperature Tm to be >48° C. The design rules follow standard protocol for the commercial NEBuilder® ligation kit (DNA assembly reagent) (New England Biolabs, Ipswich, MA, USA). Sequence as below (shown 5' to 3'):

```
                                          (SEQ ID NO: 1)
TCGAGGCCACCATGGGATATCaagatcttgacgcatcNNNNNNNNNNNNN NNNNNNNNNNNNNatcGAATTCACCCCGGGTGAAGC
```

In the above sequence, the capitalised 21 bases at the 5' end are identical in the oligo and the destination vector (referred to as the 5' overlap sequence), the Ns indicate random nucleotides representing a random library, and the capitalised 3' 20 bases are identical in the insert and destination vector (the 3' overlap sequence). The 5' 21 bases also represent a target sequence to which a blocking oligonucleotide will specifically hybridise, as explained below.

The trial oligo library was ordered as a standard, desalted oligo and as PAGE purified from Sigma Genosys (Merck KGaA, Darmstadt, Germany). The library arrived lyophilised and was re-suspended to a final concentration of 0.4 µM in 1× NEBuffer 2™ (restriction endonuclease buffer) (New England Biolabs, Ipswich, MA, USA). The library comprises a mixture of full-length and truncated oligos.

Two blocking oligos were ordered, and these are reverse complementary to the 5' 21 base overlap sequence such that they will specifically hybridise to the target sequence. One consisting of DNA oligos:

```
                                          (SEQ ID NO: 2)
     5' GATATCCCATGGTGGCCTCGA 3'
```

And the other consisting of RNA oligos:

5' GAUAUCCCAUGGUGGCCUCGA 3' (SEQ ID NO: 3)

Both sets of blocking oligos were ordered as standard, lyophilised, desalted oligos from Sigma Genosys (Merck KGaA, Darmstadt, Germany) and re-suspended to a final concentration of 0.4 µM in 1× NEBuffer 2™ (restriction endonuclease buffer) (New England Biolabs, Ipswich, MA, USA).

The desalted trial oligo library was mixed with either the RNA or the DNA 5' blocking oligo at a molar ratio of 1:1 in a total volume of 8 µl with a final concentration of 0.2 M for each oligo (both oligos were initially at 0.4 µM, so when combined each was at 0.2 µM). The library was hybridised to either oligo by incubating at 95° C. for 5 minutes (min) then to 55° C. for 30 seconds (sec). The temperature was then held at 37° C. 2 µl was removed from each reaction and 3 U RecJf (New England Biolabs, Ipswich, MA, USA) was added. RecJf is a single-strand specific 5' exonuclease, and as such digests from the 5' end of single-stranded DNA. All full-length oligos which are bound to the 5' blocking oligos will therefore not be digested by the enzyme. However, all truncated oligos (i.e. lacking the 5' target sequence), which remain single-stranded, will be digested by RecJf. The reactions were incubated at 37° C., with 2 µl removed from both reactions after 30 min, 2 hours and 4 hours. All reactions were heated to 65° C. for 20 min to inactivate the enzyme. Samples were run on a 20% precast TBE gel run at 200V for 1 hour, stained with 1× GelRed (Biotium Inc, Fremont, CA, USA) and visualised under UV.

Following visualisation of the gel, the optimal digestion time of 4 hours was selected. 2 µl of the RNA oligo blocked library was removed and the remaining reaction was digested with 5U RNase H and 25 U of RNase If (both New England BioLabs, Ipswich, MA, USA). This RNase mixture digests the RNA blocking oligo, leaving the DNA oligos unaffected. The reaction was incubated at 37° C. for 45 min and 70° C. for 20 min.

Five cloning reactions were performed using 2 µl of either:
1) undigested trial oligo library,
2) desalted DNA oligo blocked, 4 hour digested oligo library,
3) PAGE purified, oligo library,
4) RNA oligo blocked, 4 hour digested oligo library, and
5) RNA oligo blocked, 4 hour digested, RNase treated oligo library.

2 µl from each library preparation was added to 20 ng linearised destination vector in 1× NEBuilder® HiFi mix (DNA assembly reagent) (New England BioLabs, Ipswich, MA, USA) in a final volume of 10 µl. Samples were incubated at 50° C. for 1 hour. 1 µl of each of the assembled products were used to transform full aliquots of NEB 5-alpha competent *E. coli* cells as per manufacturer's protocol (New England BioLabs, Ipswich, MA, USA). Successful ligation reactions were determined by colony PCR using M13 F and M13 R standard primers which flank the trial library insert. PCR products were run for 30 min at 80V on a 1% TAE gel stained with 1× GelRed (Biotium Inc, Fremont, CA, USA). Products were visualised under UV light.

Design of Long Single-Stranded Oligo Library, Blocking Oligo and Cloning Vector

Following on from the test library discussed above, a pooled synthetic library of ssDNA oligos that tiled four enhancer sequences from H. *Sapiens* was designed as follows. The 5' and 3' ends contained 20 bases of sequence with a melting temperature of >48° C., again following the design protocol for the commercial kit NEBuilder® HiFi mix (DNA assembly reagent) (New England BioLabs, Ipswich, MA, USA). The synthetic library ranged from 192 to 199 bases in length, with an average GC content of 61%. The library was ordered from Twist BioSciences (San Francisco, CA, USA). The general sequence layout of the finished library was as follows:

5' TGGCCTAACTGGCCGGTACC > synthetic library > TCGACAGATCTGAATTCCTA 3'
(SEQ ID NO: 4)                                  (SEQ ID NO: 5)

A 5' DNA blocking oligo and a 5' RNA blocking oligo were designed reverse complementary to the 5' 20 bases of the synthetic library oligo sequence, and ordered from Sigma Genosys (Merck KGaA, Darmstadt, Germany). Blocking oligo sequences are shown below (DNA then RNA):

5' GGTACCGGCCAGTTAGGCCA 3' (SEQ ID NO: 6)

5' GGUACCGGCCAGUUAGGCCA 3' (SEQ ID NO: 7)

The blocking oligos were re-suspended to a final concentration of 0.8 UM in 1× NEBuffer 2™ (restriction endonuclease buffer) (New England BioLabs, Ipswich, MA, USA).

Figure 2:
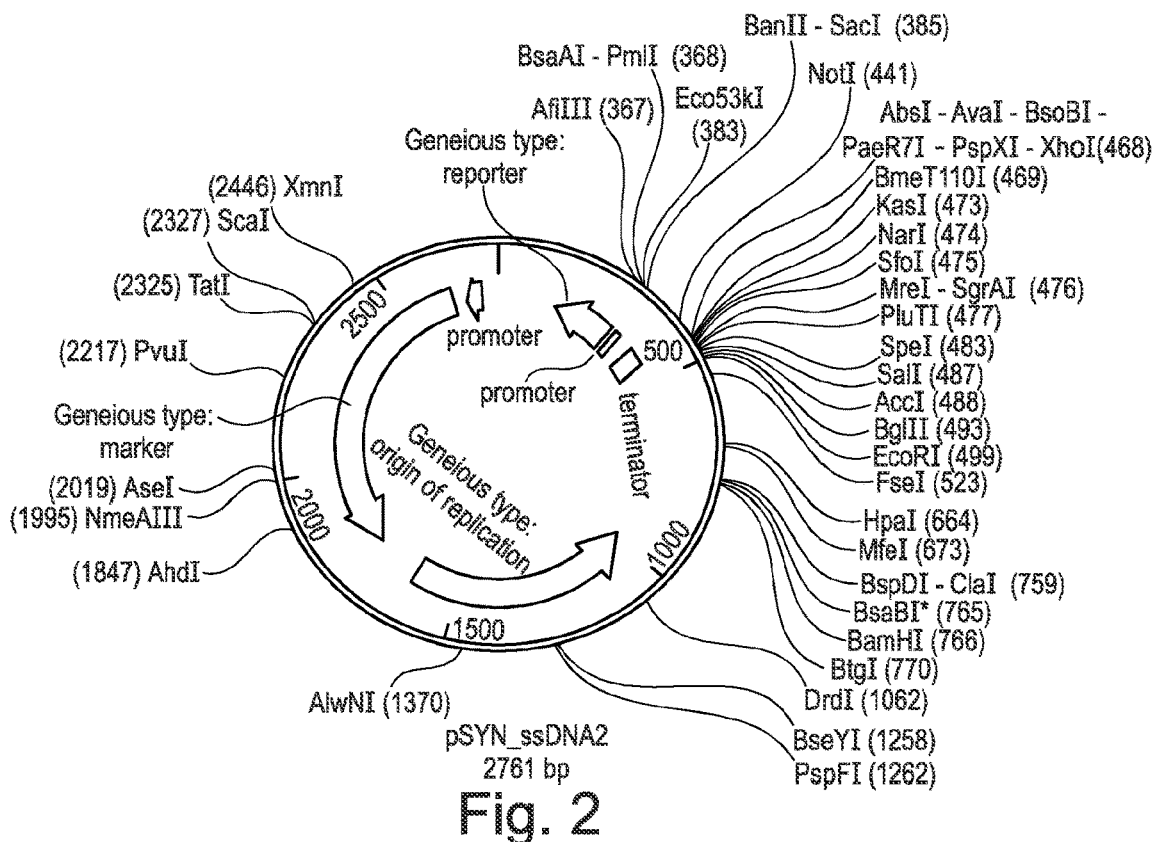
FIG. 2—plasmid map of pSYN_ssDNA2.

An in-house destination vector (pSYN_ssDNA2—sequence below and map shown in FIG. 2) based on pMA-T was designed so that digestion with Bsu36I and SpeI would create the same 20 bp sequence at the 5' and 3' ends as the sequence that flanks the library oligos. The vector was ordered from GeneArt (Thermo Fisher Scientific, Waltham, MA, USA). The vector was linearised with Bsu36I and SpeI-HF restriction enzymes (both New England BioLabs, Ipswich, MA, USA) and cleaned up using AMPure beads following standard protocol (Agencourt®AMPure® XP, Agilent, Santa Clara, CA, USA).

Enzymatic Clean-Up of Long Single-Stranded Oligo Library

Two enzymatic clean-up steps were trialled with the synthetic library as per the test library above. Briefly, the library was re-suspended to 0.8 µM in 15 µl of 1× NEBuffer 2™ (restriction endonuclease buffer) (New England BioLabs, Ipswich, MA, USA). Two clean-up methods were tested, one with the DNA blocking oligo and the other with the RNA blocking oligo. 0.8 µM of DNA blocking oligo was mixed with the synthetic library at a final equimolar ratio of 1:1. At the same time, 0.8 µM of RNA blocking oligo was also mixed with the library at an equimolar ratio. The blocking oligos were hybridised to the library by incubating at 95° C. for 5 min, then 52° C. for 30 seconds, then held at 37° C. 3U RecJf (New England BioLabs, Ipswich, MA, USA) was added and the sample was incubated at 37° C. for 4 hours after which the enzyme was inactivated at 65° C. for 20 min. RNA blocking oligo was removed by digesting with 5U RNase H and 25 U of RNase If (both New England Biolabs, Ipswich, MA, USA) at 37° C. for 45 min then at 70° C. for 20 min.

Cloning of Single-Stranded Oligo into Linearised Vector

Three cloning reactions were performed using 2 μl of either:
1) undigested synthetic library,
2) desalted DNA oligo blocked, 4 hour digested synthetic library,
3) RNA oligo blocked, 4 hour digested, RNase treated synthetic library.

2 μl of the above library preparations were added to 20 ng linearised vector (pSYN_ssDNA2) in 1× NEBuilder® HiFi mix (DNA assembly reagent) to a final volume of 10 μl. The reaction was incubated at 50° C. for 1 hour. 1 μl from each of the ligation reactions were used to transform a full aliquot of NEB 5-alpha competent E. coli cells as per manufacturer's protocol (New England Biolabs, Ipswich, MA, USA). Standard primers M13 F and M13 R were used to confirm successful ligation. Additionally, 3 colonies were selected, grown over night and plasmid DNA was purified (Qiagen Miniprep, Qiagen, Manchester, UK). Plasmids were sent to GATC Biotech (Constance, Germany) for Sanger sequencing using M13 F to check for ligation errors.

Results and Discussion

85 Base Trial Oligo Library Clean-Up and Cloning Optimisation

Figure 4:
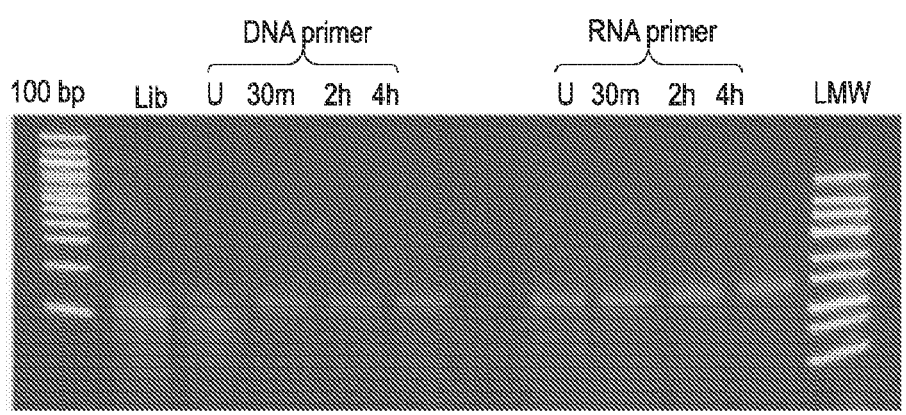
FIG. 4—gel showing RecJf exonuclease digestion to purify full-length oligos from mixed population capped with a protective 5' DNA or RNA blocking oligo. 100 bp is the 100 base pair ladder (NEB), Lib is the trial oligonucleotide library. U is undigested library hybridised to the respective blocking oligo. 30 m, 2 h and 4 h refer to the length of time samples were digested with the exonuclease. LWM shows a low weight molecular marker.

A 4-hour digestion with RecJf exonuclease removed most of the incomplete oligos, as confirmed by electrophoresis (FIG. 4). Interestingly the RNA blocking oligo appears to provide better protection from digestion than the DNA blocking oligo, although this is somewhat subjective, being based on the gel image only.

Transformation efficiencies of the five ligation reactions in Table 1 show that transformation efficiencies following enzymatic clean-up with RNA blocking oligo and RNase digestion to be around half those using a PAGE purified oligo insert. This method shows nearly a ten-fold improvement in transformation efficiencies when compared with the non-enriched trial oligo mixture.

It is important to note that for synthetic long oligonucleotides libraries (e.g. longer than 120 bases), each library member is typically present at very low concentrations (i.e. very low copy numbers). This means that they cannot be PAGE purified due to the significant losses incurred through this method. An alternative method of purification which is compatible with downstream molecular biology techniques is much needed, and is provided by the present invention.

TABLE 1

Cloning results for the five ligation reactions for the trial oligo library.

| 5' blocking oligo | None | DNA | | RNA | |
|---|---|---|---|---|---|
| Purification | Unpurified | PAGE | RecJf | RecJf | RecJf + RNase |
| TE (CFU/μg) | $4.9 \times 10^6$ | $6.1 \times 10^7$ | $1 \times 10^7$ | $9.7 \times 10^6$ | $3.2 \times 10^7$ |
| CE (%) | 81 | 100 | 94 | 100 | 100 |

TE = transformation efficiency, representing the number of bacterial cells which have successfully taken up assembled plasmids. TE is measured in colony forming units (CFU) per μg of input assembled plasmid DNA.
CE = cloning efficiency or the number of correctly assembled plasmids. CE is measured as % of correct plasmids determined by colony PCR.

Cloning Results for Long Single-Stranded Oligo Library

The cloning results for the synthetic library without enzymatic clean-up and the synthetic library cleaned-up using the DNA blocking oligo failed to generate any clones containing the library insert (Table 2). The synthetic library cleaned-up using the RNA blocking oligo contained some library inserts, however both CE and TE was low. Sequencing 3 clones predicted to contain complete ligated plasmids confirmed all clones with the insert contained the complete library sequence with no base pair changes.

TABLE 2

Cloning results for the three ligation reactions for the synthetic library.

| 5' blocking oligo | None | DNA | RNA |
|---|---|---|---|
| Purification | Unpurified | RecJf | RecJf + RNase |
| TE (CFU/μg) | N/A | N/A | $1 \times 10^6$ |
| CE (%) | 0 | 0 | 12.5 |

TE = transformation efficiency, representing the number of bacterial cells which have successfully taken up assembled plasmids. TE is measured in colony forming units (CFU) per μg of input assembled plasmid DNA.
CE = cloning efficiency or the number of correctly assembled plasmids. CE is measured as % of correct plasmids determined by colony PCR.

This method is able to clean-up and clone synthetic oligo libraries >190 bp. At the current TE and CE, however, this is not yet suitable for large scale library preparations. Given these results, at least 100 transformations would be required to generate a library of 2× the input sequences of 18 000.

Traditional oligo clean-up methods require additional purification steps before the oligo is ready for use in downstream molecular biology applications which may result in significant loss of product. Such clean-up methods are not suitable for long oligonucleotide libraries, e.g. longer than 120 bp. The enzymatic clean-up method described herein can be performed in the same tube as the ligation reaction, making use of all available full-length oligos. Therefore, the entire reaction can be used without a clean-up step to transform competent bacterial cells. This will be beneficial for other cloning methods which require longer oligos.

Example 2-Improved Clean-Up and Cloning of Long Single-Stranded Oligonucleotide into Double-Stranded Plasmid Vectors-Adding a Primer Extension Step Summary It was hypothesised that converting the single-stranded oligo to a double-stranded oligo would improve the transformation and cloning efficiency of the reaction. This is because the commercial NEBuilder® HiFi mix (DNA assembly reagent) has been optimised for use with double-stranded DNA fragments. However, the standard suggested option of using PCR to amplify the synthetic library is not recommended for synthetic libraries with high GC content and repetitive sequences as template switching can occur. Therefore, a primer extension step was performed to convert the enzymatically cleaned-up single-stranded fragment to double-stranded DNA prior to the ligation reaction.

Methods

Design of Long Single-Stranded Oligo Library, Blocking Oligo and Cloning Vector

The same single-stranded oligo library, RNA blocking oligo and cloning vector from Experiment 1 were used in this experiment. The sequences remain the same. For clarity, sequence are included below. The synthetic library sequence:

5' TGGCCTAACTGGCCGGTACC > synthetic library > TCGACAGATCTGAATTCCTA 3'
     (SEQ ID NO: 4)                              (SEQ ID NO: 5)

The 5' RNA blocking oligo, ordered from Sigma Genosys (Merck KGaA, Darmstadt, Germany):

(SEQ ID NO: 7)
5' GGUACCGGCCAGUUAGGCCA 3'

The blocking oligo was re-suspended to a final concentration of 0.8 µM in 1× NEBuffer 2™ (restriction endonuclease buffer) (New England BioLabs, Ipswich, MA, USA).

A 3' DNA primer for primer extension was designed reverse complementary to the last 20 bp of the synthetic library oligo sequence and ordered from Sigma Genosys (Merck KGaA, Darmstadt, Germany). Primer sequence below:

(SEQ ID NO: 8)
5' TAGGAATTCAGATCTGTCGA 3'

The 3' DNA primer was resuspended to 0.2 µM in 1× NEBuffer 2™ (restriction endonuclease buffer) (New England BioLabs, Ipswich, MA, USA).

The same in-house destination vector (pSYN_ssDNA2—sequence below and map shown in FIG. 2) based on pMA-T obtained from GeneArt (Thermo Fisher Scientific, Waltham, MA, USA) was used in this experiment. Bsu36I and SpeI-HF restriction enzymes (both New England BioLabs, Ipswich, MA, USA) were used to linearise the vector. Linearised vector DNA was cleaned up using AMPure beads following standard protocol (Agencourt®AMPure® XP, Agilent, Santa Clara, CA, USA).

Enzymatic Clean-Up of Long Single-Stranded Oligo Library

The library was cleaned-up using the best method from Experiment 1, namely the RNA blocking oligo and RNase digestion of the oligo. Briefly, the library was re-suspended to 0.8 µM in 15 µl of 1× NEBuffer 2™ (restriction endonuclease buffer) (New England Biolabs, Ipswich, MA, USA). 0.8 µM of RNA blocking oligo was mixed with 0.8 µM of the synthetic library. The blocking oligos were hybridised to the library by incubating at 95° C. for 5 min, then 52° C. for 30 seconds, then held at 37° C. 3U RecJf (New England Biolabs, Ipswich, MA, USA) was added and the sample was incubated at 37° C. for 4 hours after which the enzyme was inactivated at 65° C. for 20 min. RNA blocking oligo was removed by digesting with 5U RNase H and 25U of RNase If (both New England Biolabs, Ipswich, MA, USA) at 37° C. for 45 min then at 70° C. for 20 min.

Primer extension of cleaned-up long single-stranded oligo library The cleaned-up library (now at approximately 0.2 µM) was mixed with 0.2 µM of 3' DNA primer. The primer was annealed to the synthetic library by heating the oligos to 95° C. for 5 min then to 50° C. for 30 sec then held at 37° C. 5U Klenow Fragment (3'→5' exo-) (New England Biolabs, Ipswich, MA, USA) and a final concentration of 1 mM each dNTP were added. The sample was incubated at 37° C. for 4 hours, then to 65° C. for 20 min to inactivate the polymerase.

Cloning of Primer Extended Long Single-Stranded Oligo into Linearised Vector

Cloning was performed as per Experiment 1. In 1× NEBuilder® HiFi mix (DNA assembly reagent), 20 ng linearised vector (pSYN_ssDNA2) and 2 µl from the prepared library were mixed to a final volume of 10 µl. The reaction was incubated at 50° C. for 1 hour. A full aliquot of NEB 5-alpha competent *E. coli* cells was transformed with 1 µl of the ligation reaction following manufacturer's protocol (New England Biolabs, Ipswich, MA, USA). Successful ligation reaction was confirmed with colony PCR using standard primers M13 F and M13 R. Additionally, 10 colonies predicted to contain the library insert were grown over night and plasmid DNA was purified (Qiagen Miniprep, Qiagen, Manchester, UK). Plasmids were sent to GATC Biotech (Constance, Germany) for Sanger sequencing using M13 F to check for ligation errors.

Results and Discussion

Cloning Results for Primer Extended, Long Single-Stranded Oligo Library

The addition of a primer extension step resulted in a transformation efficiency of $9 \times 10^6$ cfu/µg with a cloning efficiency of 55.5% (20/36 clones) as determined from colony PCR. Sequencing 10 clones predicted to contain complete ligated plasmids confirmed that all clones with the insert contained the library sequence. Three contained the library sequence without any base pair changes, three contained the library sequence with one single base pair change, three contained between 2 and 4 base pair changes and two were severely truncated (deletions of >10 base pairs). This is presumably due to the low fidelity of the Klenow Fragment (3'→5' exo-) which lacks proof-reading ability. The addition of a primer extension step improves cloning in terms of transformation and cloning efficiency compared to the results from Experiment 1, however there is still a need for improvement if the synthetic library is to be cloned without errors.

Example 3—Clean-Up and Cloning of Long Single-Stranded Oligonucleotides into Double-Stranded Plasmid Vectors-Testing the Addition of SSBP Summary Long ssDNA oligos are prone to secondary structure, therefore it was hypothesised that the addition of a single-stranded binding protein (SSBP) would be beneficial to improve the clean-up step of the reaction. This protein is also documented to assist the RecJf enzyme in digestion of shorter oligos (Han et al. 2006—Nucleic Acids Research, 2006, Vol. 34, No. 4, 1084-1091). However, it was unclear how this protein would affect the clean-up and downstream cloning process.

Methods

A new trial oligo of 109 bases was designed with 20 bases of neutral sequence with a melting temperature of >48° C. in the 5' and 3' ends, as per the experiment discussed above and following the design protocol for the commercial kit NEBuilder® (DNA assembly reagent) (New England Biolabs, Ipswich, MA, USA). Sequence as below:

(SEQ ID NO: 9)
5' TGCGTTGGACACTATCAATCtaagccgtccaggacacggatctggac agcga-N$_{20}$-tgagctctgggaggcgaTCGACAGATCTGAATTCCTA 3'

The first capitalised 20 bases in the 5' end are identical in the oligo and the destination vector (the 5' overlap sequence), and also represent the target sequence for the blocking oligo. The Ns indicate random nucleotides and represent a random library, and the 3' 20 bases that are identical in the insert and destination vector (the 3' overlap sequence) are also capitalised. The trial oligo library was ordered as a standard, desalted oligo from Sigma Genosys (Merck KGaA, Darmstadt, Germany). The library arrived lyophilised and was re-suspended to a final concentration of 0.4 µM in 1× NEBuffer 2™ (restriction endonuclease buffer) (New England Biolabs, Ipswich, MA, USA).

A 5' RNA blocking oligo was designed reverse complementary to the 5' 20 bases of the trial oligo library sequence, and ordered from Sigma Genosys (Merck KGaA, Darmstadt, Germany). Blocking oligo sequence below:

(SEQ ID NO: 10)
5' GAUUGAUAGUGUCCAACGCA 3'

The RNA blocking oligo was re-suspended to a final concentration of 0.4 µM in 1× NEBuffer 2™ (restriction endonuclease buffer) (New England BioLabs, Ipswich, MA, USA).

Figure 3:
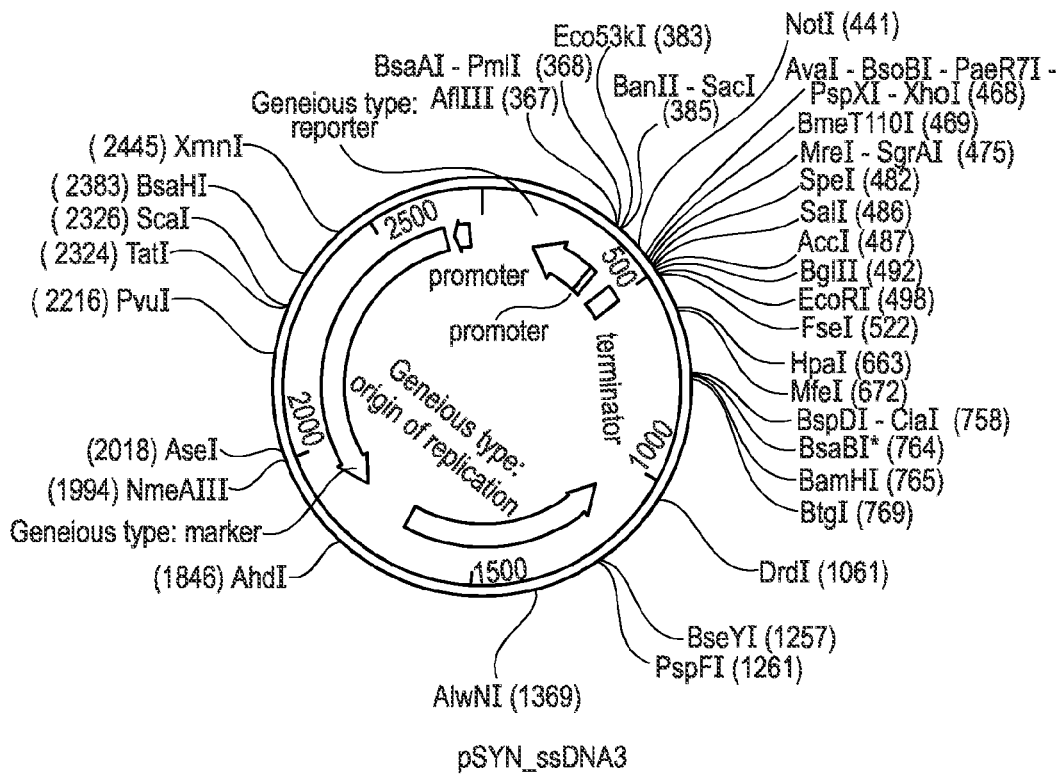
FIG. 3—plasmid map of pSYN_ssDNA3.

An in-house destination vector (pSYN_ssDNA3-sequence below and map shown in FIG. 3) based on pMA-T was designed so that digestion with XhoI and SpeI would create the same 20 bp sequence at the 5' and 3' ends as the sequence that flanks the library oligos. The vector was ordered from GeneArt (Thermo Fisher Scientific, Waltham, MA, USA). The vector was linearised with XhoI and SpeI-HF restriction enzymes (both New England BioLabs, Ipswich, MA, USA) and cleaned up using AMPure beads following standard protocol (Agencourt®AMPure® XP, Agilent, Santa Clara, CA, USA).

The trial oligo library and the RNA blocking oligo were mixed at a ratio of 1:1 in a total volume of 40 µl with a final concentration of 0.2 µM for each oligo.

Seven reactions were set up at the same time to optimise the concentration of SSB protein for the enzymatic clean-up and ligation reactions. Three reactions of different concentrations at the enzymatic clean-up step, three reactions where the SSB protein was added at the ligation reaction step and a final control reaction where the trial oligo library was cleaned-up and ligated without any SSBP.

40 ng, 80 ng or 120 ng of ET SSB (New England Biolabs, Ipswich, MA, USA) was mixed with 8 µl of trial library and RNA blocking oligo in three separate reactions (final concentrations of each oligo 0.16 µM). These three reactions and the remaining trial library and blocking oligo mix (adjusted to a final concentration of 0.16 µM for each oligo) were incubated at 95° C. for 5 min then to 55° C. for 30 sec to hybridise the blocking oligo to the library. The temperature was then held at 37° C. and 3U RecJf (New England Biolabs, Ipswich, MA, USA) was added to each reaction. The reaction was incubated at 37° C. for 4 hours with an inactivation step of 65° C. for 20 min. The RNA blocking oligo was removed from all reactions by digesting with 5U RNase H and 25U of RNase If (both New England Biolabs, Ipswich, MA, USA). The reactions were incubated at 37° C. for 45 min and 70° C. for 20 min. Reactions were stored at −20° C. overnight.

Seven ligation reactions were performed using the commercial NEBuilder® (DNA assembly reagent) kit (New England Biolabs, Ipswich, MA, USA). For the three enzymatic clean-up reactions with SSB protein and for the control reaction, 2 µl from each clean-up reaction was added to 20 ng linearised destination vector (pSYN_ssDNA3, prepared as before) in 1× NEBuilder® HiFi mix (DNA assembly reagent) (New England Biolabs, Ipswich, MA, USA) in a final volume of 10 µl. Three additional reactions were set up to test the concentration of SSB protein added at the ligation reaction step. Enzymatically cleaned library, 20 ng linearised vector and 8 ng, 16 ng or 24 ng SSB protein was mixed in 1× NEBuilder® HiFi mix (DNA assembly reagent) (New England Biolabs, Ipswich, MA, USA) in a final volume of 10 µl. The amount of SSB protein added at the ligation step was equivalent to the total protein in the ligation reaction for the three reactions with the SSB protein added at the clean-up step. Samples were incubated at 50° C. for 1 hour.

1 µl of each of the assembled products were used to transform half aliquots (25 µl) of NEB 5-alpha competent E. coli cells as per manufacturer's protocol (New England BioLabs, Ipswich, MA, USA). Successful ligation reactions were determined by colony PCR using M13 F and M13 R primers, as before. PCR products were run for 30 min at 80V on a 1% TAE gel stained with 1× GelRed (Biotium Inc, Fremont, CA, USA) and visualised under UV light.

Testing the Inclusion of a Primer Extension Step in the Cloning Reaction

The following work was conducted to test the hypothesis that converting the single-stranded oligo library to a double stranded (ds) library prior to the ligation reaction might further improve the cloning process. The commercial NEBuilder® (DNA assembly reagent) kit can be used to ligate ss oligos, but the reaction mix has been primarily optimised for use with long (>1 kb) ds DNA fragments. Thus, the commercial NEBuilder® (DNA assembly reagent) kit was hypothesised to be sub-optimal for ligation of single-stranded oligos into a vector.

Following the results of the SSB protein optimisation experiment, a second optimisation step was performed to test if a primer extension step after the enzymatic clean-up and before the ligation reaction would increase the cloning efficiency. Two different polymerases, one not considered to have strand displacement activity and with a high 3' exonuclease activity, Phusion HF, and one with moderate strand displacement activity and without any exonuclease activity, Klenow Fragment (3'→5' exo-) were used to test the addition of a primer extension step.

A 3' DNA primer was designed reverse complementary to the 3' 20 base overlap sequence and ordered from Sigma Genosys (Merck KGaA, Darmstadt, Germany) as previously. Primer sequence below:

(SEQ ID NO: 8)
5' TAGGAATTCAGATCTGTCGA 3'

The primer was re-suspended in dH₂O to 10 µM.

The two optimal SSB protein conditions from the previous experiment (120 ng SSB protein addition to the enzymatic clean-up method, and 8 ng SSB protein addition to the ligation reaction) were used to test the primer extension with the two polymerases (four reactions set up in total). Primer extension was performed with 0.3 µM enzymatically enriched library from the above experiments, 1 µM final concentration 3' DNA primer, 0.2 U Phusion HF polymerase (New England Biolabs, Ipswich, MA, USA) or 5 U Klenow Fragment (3'→5' exo-) (New England Biolabs, Ipswich, MA, USA). Reactions were performed in 1× polymerase specific PCR buffer with 1 mM final concentration of each dNTP. The two reactions with the Phusion polymerase were mixed on ice and then incubated at 98° C. for 30 sec, 57° C. for 30 sec and 72° C. for 5 min then down to 4° C. hold. The reactions run with the Klenow fragment (3'→5' exo-) were mixed on ice without the Klenow fragment as this is heat sensitive. Reactions were incubated at 95° C. for 5 min, 50° C. for 30 sec the held at 37° C., when the Klenow fragment was added to the reaction. The sample was incubated at 37° C. for 1 hour then the enzyme was inactivated at 65° C. for 20 min.

2 µl from each of the four different primer extension reactions was mixed with 20 ng linearised vector in 1× NEBuilder® HiFi mix (DNA assembly reagent) in a total volume of 10 µl, as before. Samples were incubated at 50° C. for 1 hour. Following assembly, 1 µl from each reaction were used to transform half aliquots (25 µl) of NEB 5-alpha competent E. coli cells as per manufacturer's protocol (New England Biolabs, Ipswich, MA, USA). Successful ligation reactions were again determined by colony PCR with M13 F and M13 R primers. PCR products were run for 30 min at 80 V on a 1% TAE gel stained with 1× GelRed (Biotium Inc, Fremont, CA, USA) and visualised under UV light.

Results and Discussion

The Effects of Adding SSBP to the Enzymatic Clean-Up Method

As only half an aliquot of NEB 5-alpha cells was transformed in this trial experiment the results cannot be directly compared to the other experiments with the enzymatic clean-up method discussed above. While the transformation efficiency of this experiment appears less than that of the first experiment (see Table 3), the results are not directly comparable. Compared to the control reaction without any SSB protein, all reactions including SSB resulted in a ten-fold increase in transformation efficiency. The addition of 120 ng and 80 ng SSB protein at the clean-up step resulted in the highest transformation efficiencies for the three reactions where SSB protein was added at the clean-up step, and the addition of 8 ng of SSB protein added at the ligation reaction step resulted in the highest transformation efficiency and most correct ligation constructs. It appears that the SSB protein is assisting with the RecJf digestion of truncated oligos, and it is presumed that that this is achieved at least in part by eliminating secondary structure in the library oligos and by facilitating binding of the RNA blocking oligo to the 5' end of the library oligos. Surprisingly, however, binding of the SSB protein does not disrupt binding of the blocking oligo as might be expected. Thus, despite the presence of SSB protein, the blocking oligo is able to bind to, and protect, the target single-stranded nucleic acids.

TABLE 3

Cloning results for the SSB protein addition to the enzymatic clean-up method.

| SSB added | At clean-up | | | At ligation | | | Control |
|---|---|---|---|---|---|---|---|
| SSB conc. | 120 ng | 80 ng | 40 ng | 24 ng | 16 ng | 8 ng | None |
| TE (CFU/µg) | 5.2 × 10⁶ | 5 × 10⁶ | 4.6 × 10⁶ | 3.5 × 10⁵ | 1.2 × 10⁶ | 6.2 × 10⁶ | 7 × 10⁵ |
| CE (%) | 100 | 75 | 63 | 88 | 88 | 88 | 100 |

TE = transformation efficiency measured in colony forming units (CFU) per µg of input DNA.
CE = cloning efficiency measured as % of correct plasmids determined by colony PCR.

The Primer Extension Addition to the Single-Stranded Binding Protein Experiment

The addition of a primer extension step improved the transformation efficiency and the cloning accuracy of the initial SSB protein experiment (see Table 4). As discussed above, this likely reflects the fact that the NEBuilder® (DNA assembly reagent) commercial mix was optimised for ligating ds DNA fragments.

TABLE 4

Cloning results for the SSB protein addition to the enzymatic clean-up method.

| Polymerase | Phusion | | Klenow exo - | |
|---|---|---|---|---|
| SSB | 120 ng | 8 ng | 120 ng | 8 ng |
| TE (CFU/µg) | 9.5 × 10⁶ | 7.2 × 10⁶ | 3.0 × 10⁶ | 7.5 × 10⁶ |
| CE (%) | 75 | 88 | 100 | 88 |

TE = transformation efficiency measured in colony forming units (CFU) per µg of input DNA.
CE = cloning efficiency measured as % of correct plasmids determined by colony PCR.

Extension with Phusion HF polymerase nearly doubled the transformation efficiency of the reaction with 120 ng SSB protein added at the clean-up step. The reaction with 8 ng SSB protein added at the primer extension step was improved by 1×10⁶ cfu/µg. Primer extension using the Klenow fragment also improved the ligation reaction when 8 ng of SSB protein was added at the primer extension step by 1×10⁶ cfu/µg. However, when 120 ng SSB protein was added at the clean-up step the primer extension reaction did not improve the cloning. In the cloning reaction, the concentration of SSB protein is equivalent to the test reaction with 24 ng SSB protein added at this stage. It is possible that this concentration of SSB protein hinders rather than assists the reaction.

Phusion HF polymerase has high 3' exonuclease activity, therefore the increased number of incorrect inserts compared to the Klenow fragment can be assumed may result from this. No Sanger sequencing was performed on the assembled ligation products, so the extent of the errors the polymerases may have introduced into the library is not known.

Example 4—Clean-Up and Cloning Long Single-Stranded Oligonucleotides into Double Stranded Plasmid Vectors with the Addition of a Primer Extension Step and a SSBP Methods Design of Long Single-Stranded Oligo Library, Blocking Oligo and Cloning Vector A pooled synthetic library of ssDNA oligos that tiled four enhancer sequences from H. Sapiens was designed as follows. The 5' and 3' ends contained 20 bases of sequence with a melting temperature of >48° C., again following the design protocol for the commercial kit NEBuilder® (DNA assembly reagent) (New England BioLabs, Ipswich, MA, USA). The synthetic library ranged from 192 to 199 bases in length, with an average GC content of 61%. The library was ordered from Twist BioSciences (San Francisco, CA, USA). The general sequence layout of the finished library was as follows:

```
5' TGCGTTGGACACTATCAATC > synthetic library > TCGACAGATCTGAATTCCTA 3'
    (SEQ ID NO: 11)                           (SEQ ID NO: 5)
```

Destination vector pSYN_ssDNA3, based on pMA-T and ordered from GeneArt was again used. The vector was linearised with XhoI and SpeI-HF (both New England Biolabs, Ipswich, MA, USA). Linearised vector was purified with AMPure beads following standard protocol (Agencourt®AMPure® XP, Agilent, Santa Clara, CA, USA).

The same 5' RNA blocking oligo was used, which is reverse complementary to the first 20 bases of the synthetic library sequence and ordered from Sigma Genosys (Merck KGaA, Darmstadt, Germany). Blocking oligo sequence:

```
                                     (SEQ ID NO: 10)
    5' GAUUGAUAGUGUCCAACGCA 3'
```

The RNA blocking oligo was re-suspended to a final concentration of 0.7 μM in 1× NEBuffer 2™ (restriction endonuclease buffer) (New England Biolabs, Ipswich, MA, USA).

Enzymatic Clean-Up of Long Single-Stranded Oligo Library

The synthetic library was cleaned-up using the enzymatic clean-up method determined for the test library above. Briefly, the library was re-suspended in 0.7 μM of RNA blocking oligo such that the final ratio of blocking oligos to library oligos was 1:1 (i.e. equimolar). The blocking oligo was hybridised to the library by incubating at 95° C. for 5 min, then 52° C. for 30 seconds, then held at 37° C. 3U RecJf was added and the sample was incubated at 37° C. for 4 hours after which the enzyme was inactivated at 65° C. for 20 min. RNA blocking oligo was removed by digesting with 5 U RNase H and 25 U of RNase If (both New England Biolabs, Ipswich, MA, USA) at 37° C. for 45 min then at 70° C. for 20 min.

Cloning of Single-Stranded Oligo into Linearised Vector

Cloning was performed with two additional steps. Secondary structure can be a problem with long single-stranded oligos. Therefore, a single-stranded binding protein (SSBP) was added to the reaction. Additionally, a primer extension step was performed to convert the ssDNA to dsDNA to maximise the cloning efficiency.

Cleaned oligo library was mixed with 10 ng ET SSB (New England Biolabs, Ipswich, MA, USA), 0.2 U Phusion HF polymerase (New England Biolabs, Ipswich, MA, USA) and 1 μM 3' DNA primer. Sample was incubated at 98° C. for 30 sec, 57° C. for 30 sec, 72° C. for 5 min.

2 μl primer extended library was added to 20 ng linearised vector (pSYN_ssDNA3) in 1× NEBuilder® HiFi mix (DNA assembly reagent) to a final volume of 10 μl. The reaction was incubated at 50° C. for 1 hour. 1 μl of the ligation reaction was used to transform a full aliquot of NEB 5-alpha competent E. coli cells as per manufacturer's protocol (New England Biolabs, Ipswich, MA, USA). Standard primers M13 F and M13 R were used to confirm successful ligation. Additionally, 6 colonies were selected, grown over night and plasmid DNA was purified (Qiagen Miniprep, Qiagen, Manchester, UK). Plasmids were Sanger sequenced at GATC Biotech (Constance, Germany) using M13 F.

Results and Discussion

Cloning Results for Long Single-Stranded Oligo Library

The transformation efficiency for the long single-stranded oligo library was $6.5 \times 10^6$ cfu/μg with a cloning efficiency of 93.5% (15/16 clones) as determined from colony PCR. Sequencing 6 clones predicted to contain complete ligated plasmids confirmed that all clones with the insert contained the complete library sequence without any base pair changes. All sequences successfully cloned have a GC content above 65%. This shows that this clean-up method allows for the successful cloning of sequences with high GC content. It is probable that the addition of the SSB at the blocking oligo extension step at least partially facilitates this step. The transformation and cloning efficiency of this method which includes both the SSB protein and a primer extension step are sufficient to allow for cloning of the long single-stranded synthetic oligo library of 18 000 sequences at 3× with 4 ligation reactions and 40 transformations.

Overall Summary of Method

Figure 5:
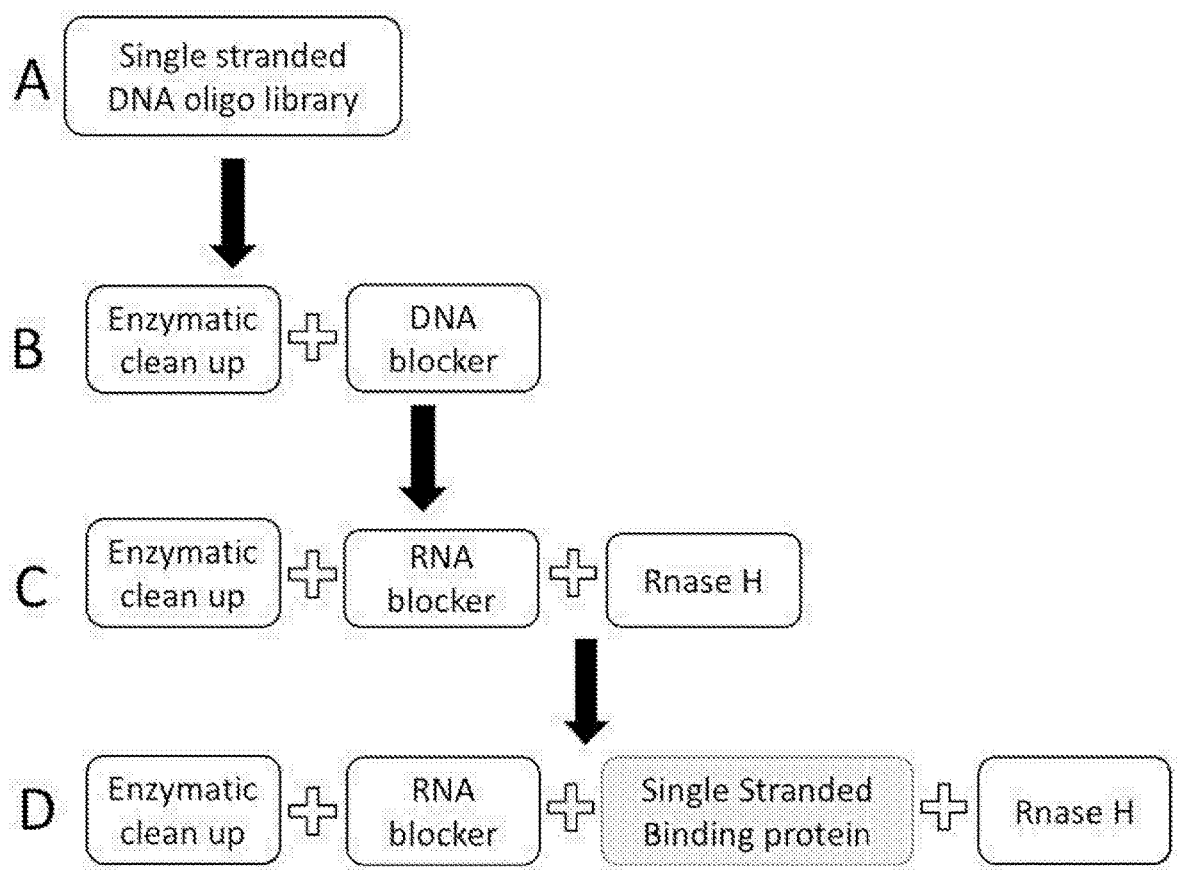
FIG. 5—shows a schematic representation of methods of enriching target single-stranded nucleic acids according to the present invention.

FIG. 5 summarises some of the key findings of the work discussed above, and the evolution of the enrichment (clean-up) method of the present invention.

FIG. 5A represents a single-stranded DNA oligo library that includes full-length (target) and truncated (non-target) oligos. The library has been created by oligo synthesis. Amplification of the target sequences by PCR is not appropriate due to the nature of the library. "Clean up" in order to enrich the target oligos relative to the non-target oligos is desirable to improve downstream molecular biology procedures, especially cloning the oligo library into a vector. When the library is cloned in this un-enriched form, poor transformation and cloning efficiency is achieved. Enrichment results in a significant improvement.

FIG. 5B represents an enzymatic enrichment (clean-up) of the library to enrich the library for the target, full-length oligos that comprise the target sequence for the blocking oligo. In this case, a DNA blocking oligo was used to protect the target oligos from digestion by the single-strand specific 5' exonuclease. The results indicate that the DNA blocking oligo allowed for protection of the target oligos and digestion of target oligos, but it was suboptimal in terms of transformation efficiency and cloning efficiency (see Table 1).

FIG. 5C represents the situation where an RNA blocking oligo was used instead of the DNA blocking oligo of 5B, followed by digestion of the RNA blocking oligo after the non-target oligos have been digested using an RNase. This resulted in a significant increase in transformation efficiency and cloning efficiency compared to the DNA blocking oligo (see Table 1).

FIG. 5D represents a further optional addition to the method of FIG. 5C, where a single-stranded DNA binding protein (SSBP) is added in addition to the use of an RNA blocking oligo and digestion of the blocking oligo by RNase. The use of SSBP appeared to resulted improvements in transformation and cloning efficiency. The presence of SSBP during the clean-up step may enhance the activity of the single-strand specific 5' exonuclease, thus better removing truncated oligos. The presence of SSBP is also likely to be beneficial in subsequent cloning steps.

Sequence Info pSYN_ssDNA1:
(SEQ ID NO: 12)

tcgaggccaccatgggatatcaagatcttgacgcgtaggaattcaccccgggtgaagctggcgtaatc atggtcatagctgtttcctgtgtgaaattgttatccgctcacaattccacacaacatacgagccggaa gcataaagtgtaaagcctggggtgcctaatgagtgagctaactcacattaattgcgttgcgctcactg cccgctttccagtcgggaaacctgtcgtgccagctgcattaatgaatcggccaacgcgcggggagagg cggtttgcgtattgggcgctcttccgcttcctcgctcactgactcgctgcgctcggtcgttcggctgc ggcgagcggtatcagctcactcaaaggcggtaatacggttatccacagaatcaggggataacgcagga aagaacatgtgagcaaaaggccagcaaaaggccaggaaccgtaaaaaggccgcgttgctggcgttttt ccataggctccgcccccctgacgagcatcacaaaaatcgacgctcaagtcagaggtggcgaaacccga caggactataaagataccaggcgtttccccctggaagctccctcgtgcgctctcctgttccgaccctg ccgcttaccggatacctgtccgcctttctcccttcgggaagcgtggcgctttctcatagctcacgctg taggtatctcagttcggtgtaggtcgttcgctccaagctgggctgtgtgcacgaaccccccgttcagc ccgaccgctgcgccttatccggtaactatcgtcttgagtccaacccggtaagacacgacttatcgcca ctggcagcagccactggtaacaggattagcagagcgaggtatgtaggcggtgctacagagttcttgaa gtggtggcctaactacggctacactagaagaacagtatttggtatctgcgctctgctgaagccagtta ccttcggaaaaagagttggtagctcttgatccggcaaacaaaccaccgctggtagcggtggtttttt gtttgcaagcagcagattacgcgcagaaaaaaaggatctcaagaagatcctttgatcttttctacggg gtctgacgctcagtggaacgaaaactcacgttaagggattttggtcatgagattatcaaaaaggatct tcacctagatccttttaaattaaaaatgaagttttaaatcaatctaaagtatatatgagtaaacttgg tctgacagttaccaatgcttaatcagtgaggcacctatctcagcgatctgtctatttcgttcatccat agttgcctgactccccgtcgtgtagataactacgatacgggagggcttaccatctggccccagtgctg caatgataccgcgagacccacgctcaccggctccagatttatcagcaataaaccagccagccggaagg gccgagcgcagaagtggtcctgcaactttatccgcctccatccagtctattaattgttgccgggaagc tagagtaagtagttcgccagttaatagtttgcgcaacgttgttgccattgctacaggcatcgtggtgt cacgctcgtcgtttggtatggcttcattcagctccggttcccaacgatcaaggcgagttacatgatcc cccatgttgtgcaaaaaagcggttagctccttcggtcctccgatcgttgtcagaagtaagttggccgc agtgttatcactcatggttatggcagcactgcataattctcttactgtcatgccatccgtaagatgct tttctgtgactggtgagtactcaaccaagtcattctgagaatagtgtatgcggcgaccgagttgctct tgcccggcgtcaatacgggataataccgcgccacatagcagaactttaaaagtgctcatcattggaaa acgttcttcggggcgaaaactctcaaggatcttaccgctgttgagatccagttcgatgtaacccactc gtgcacccaactgatcttcagcatcttttactttcaccagcgtttctgggtgagcaaaaacaggaagg caaaatgccgcaaaaaagggaataagggcgacacggaaatgttgaatactcatactcttcctttttca atattattgaagcatttatcagggttattgtctcatgagcggatacatatttgaatgtatttagaaaa ataaacaaataggggttccgcgcacatttccccgaaaagtgccacctgacgtctaagaaaccattatt atcatgacattaacctataaaaataggcgtatcacgaggccctttcgtctcgcgcgtttcggtgatga cggtgaaaacctctgacacatgcagctcccggagacggtcacagcttgtctgtaagcggatgccggga gcagacaagcccgtcagggcgcgtcagcgggtgttggcgggtgtcggggctggcttaactatgcggca tcagagcagattgtactgagagtgcaccatatgcggtgtgaaataccgcacagatgcgtaaggagaaa ataccgcatcaggcgccattcgccattcaggctgcgcaactgttgggaagggcgatcggtgcgggcct cttcgctattacgccagctggcgaaagggggatgtgctgcaaggcgattaagttgggtaacgccaggg -continued ttttcccagtcacgacgttgtaaaacgacggccagtg pSYN_ssDNA2:

(SEQ ID NO: 13)

cctaaattgtaagcgttaatattttgttaaaattcgcgttaaattttttgttaaatcagctcatttttt aaccaataggccgaaatcggcaaaatcccttataaatcaaaagaatagaccgagatagggttgagtgg ccgctacagggcgctcccattcgccattcaggctgcgcaactgttgggaagggcgtttcggtgcgggc ctcttcgctattacgccagctggcgaaagggggatgtgctgcaaggcgattaagttgggtaacgccag ggttttcccagtcacgacgttgtaaaacgacggccagtgagcgcgacgtaatacgactcactataggg cgaattggcggaaggccgtcaaggccacgtgtcttgtccagagctcgcataataaaatatctttattt tcattacatctgtgtgttggtttttgtgtggcggccgcgtggcctaactggccggtacctcgaggcg ccggcgactagtcgacagatctgaattcctagagtcggggcggccggccgcttcgagcagacatgata agatacattgatgagtttggacaaaccacaactagaatgcagtgaaaaaaatgctttatttgtgaaat ttgtgatgctattgctttatttgtaaccattataagctgcaataaacaagttaacaacaacaattgca ttcattttatgtttcaggttcaggggaggtgtgggaggttttttaaagcaagtaaaacctctacaaa tgtggtaaaatcgataaggatccgtggtacctggagcacaagactggcctcatgggccttccgctcac tgcccgctttccagtcgggaaacctgtcgtgccagctgcattaacatggtcatagctgtttccttgcg tattgggcgctctccgcttcctcgctcactgactcgctgcgctcggtcgttcgggtaaagcctgggt gcctaatgagcaaaaggccagcaaaaggccaggaaccgtaaaaaggccgcgttgctggcgttttccca taggctccgcccccctgacgagcatcacaaaaatcgacgctcaagtcagaggtggcgaaacccgacag gactataaagataccaggcgtttccccctggaagctccctcgtgcgctctcctgttccgaccctgccg cttaccggatacctgtccgcctttctcccttcgggaagcgtggcgctttctcatagctcacgctgtag gtatctcagttcggtgtaggtcgttcgctccaagctgggctgtgtgcacgaaccccccgttcagcccg accgctgcgccttatccggtaactatcgtcttgagtccaacccggtaagacacgacttatcgccactgg cagcagccactggtaacaggattagcagagcgaggtatgtaggcggtgctacagagttcttgaagtgg tggcctaactacggctacactagaagaacagtatttggtatctgcgctctgctgaagccagttacctt cggaaaaagagttggtagctcttgatccggcaaacaaaccaccgctggtagcggtggttttttgttt gcaagcagcagattacgcgcagaaaaaaggatctcaagaagatcctttgatcttttctacggggtct gacgctcagtggaacgaaaactcacgttaagggattttggtcatgagattatcaaaaaggatcttcac ctagatccttttaaattaaaaatgaagttttaaatcaatctaaagtatatatgagtaaacttggtctg acagttaccaatgcttaatcagtgaggcacctatctcagcgatctgtctatttcgttcatccatagtt gcctgactccccgtcgtgtagataactacgatacgggagggcttaccatctggccccagtgctgcaat gataccgcgagaaccacgctcaccggctccagatttatcagcaataaaccagccagccggaagggccg agcgcagaagtggtcctgcaactttatccgcctccatccagtctattaattgttgccgggaagctaga gtaagtagttcgccagttaatagtttgcgcaacgttgttgccattgctacaggcatcgtggtgtcacg ctcgtcgtttggtatggcttcattcagctccggttcccaacgatcaaggcgagttacatgatccccca tgttgtgcaaaaaagcggttagctccttcggtcctccgatcgttgtcagaagtaagttggccgcagtg ttatcactcatggttatggcagcactgcataattctcttactgtcatgccatccgtaagatgcttttc tgtgactggtgagtactcaaccaagtcattctgagaatagtgtatgcggcgaccgagttgctcttgcc ggcgtcaatacgggataataccgcgccacatagcagaactttaaaagtgctcatcattggaaaacgt tcttcggggcgaaaactctcaaggatcttaccgctgttgagatccagttcgatgtaacccactcgtgc acccaactgatcttcagcatcttttactttcaccagcgtttctgggtgagcaaaaacaggaaggcaaa -continued atgccgcaaaaaagggaataagggcgacacggaaatgttgaatactcatactcttccttttttcaatat tattgaagcatttatcagggttattgtctcatgagcggatacatatttgaatgtatttagaaaaataa acaaatagggggttccgcgcacatttccccgaaaagtgcca pSYN_ssDNA3:

(SEQ ID NO: 14)

cctaaattgtaagcgttaatattttgttaaaattcgcgttaaattttttgttaaatcagctcatttttt aaccaataggccgaaatcggcaaaatcccttataaatcaaaagaatagaccgagataggggttgagtgg ccgctacagggcgctcccattcgccattcaggctgcgcaactgttgggaagggcgtttcggtgcgggc ctcttcgctattacgccagctggcgaaagggggatgtgctgcaaggcgattaagttgggtaacgccag ggttttcccagtcacgacgttgtaaaacgacggccagtgagcgcgacgtaatacgactcactataggg cgaattggcggaaggccgtcaaggccacgtgtcttgtccagagctcgcataataaaatatctttattt tcattacatctgtgtgttggtttttttgtgtggcggccgcgtgcgttggacactatcaatctcgagcgc cggcgactagtcgacagatctgaattcctagagtcggggcggccggccgcttcgagcagacatgataa gatacattgatgagtttggacaaaccacaactagaatgcagtgaaaaaaatgctttatttgtgaaatt tgtgatgctattgctttatttgtaaccattataagctgcaataaacaagttaacaacaacaattgcat tcattttatgtttcaggttcaggggggaggtgtgggaggttttttaaagcaagtaaaacctctacaaat gtggtaaaatcgataaggatccgtggtacctggagcacaagactggcctcatgggccttccgctcact gcccgctttccagtcgggaaacctgtcgtgccagctgcattaacatggtcatagctgtttccttgcgt attgggcgctctccgcttcctcgctcactgactcgctgcgctcggtcgttcgggtaaagcctggggtg cctaatgagcaaaaggccagcaaaaggccaggaaccgtaaaaaggccgcgttgctggcgtttttccat aggctccgcccccctgacgagcatcacaaaaatcgacgctcaagtcagaggtggcgaaacccgacagg actataaagataccaggcgtttccccctggaagctccctcgtgcgctctcctgttccgaccctgccgc ttaccggatacctgtccgcctttctcccttcgggaagcgtggcgctttctcatagctcacgctgtagg tatctcagttcggtgtaggtcgttcgctccaagctgggctgtgtgcacgaaccccccgttcagcccga ccgctgcgccttatccggtaactatcgtcttgagtccaacccggtaagacacgacttatcgccactgg cagcagccactggtaacaggattagcagagcgaggtatgtaggcggtgctacagagttcttgaagtgg tggcctaactacggctacactagaagaacagtatttggtatctgcgctctgctgaagccagttacctt cggaaaaagagttggtagctcttgatccggcaaacaaaccaccgctggtagcggtggtttttttgttt gcaagcagcagattacgcgcagaaaaaaaggatctcaagaagatcctttgatcttttctacggggtct gacgctcagtggaacgaaaactcacgttaagggattttggtcatgagattatcaaaaaggatcttcac ctagatcctttttaaattaaaaatgaagttttaaatcaatctaaagtatatatgagtaaacttggtctg acagttaccaatgcttaatcagtgaggcacctatctcagcgatctgtctatttcgttcatccatagtt gcctgactccccgtcgtgtagataactacgatacgggagggcttaccatctggccccagtgctgcaat gataccgcgagaaccacgctcaccggctccagatttatcagcaataaaccagccagccggaagggccg agcgcagaagtggtcctgcaactttatccgcctccatccagtctattaattgttgccgggaagctaga gtaagtagttcgccagttaatagtttgcgcaacgttgttgccattgctacaggcatcgtggtgtcacg ctcgtcgtttggtatggcttcagctccggttcccaacgatcaaggcgagttacatgatcccccca tgttgtgcaaaaaagcggttagctccttcggtcctccgatcgttgtcagaagtaagttggccgcagtg ttatcactcatggttatggcagcactgcataattctcttactgtcatgccatccgtaagatgcttttc tgtgactggtgagtactcaaccaagtcattctgagaatagtgtatgcggcgaccgagttgctcttgcc cggcgtcaatacgggataataccgcgccacatagcagaactttaaaagtgctcatcattggaaaacgt tcttcggggcgaaaactctcaaggatcttaccgctgttgagatccagttcgatgtaacccactcgtgc acccaactgatcttcagcatcttttactttcaccagcgtttctgggtgagcaaaaacaggaaggcaaa atgccgcaaaaaagggaataagggcgacacggaaatgttgaatactcatactcttccttttcaatat tattgaagcatttatcagggttattgtctcatgagcggatacatatttgaatgtatttagaaaaataa acaaatagggggttccgcgcacatttccccgaaaagtgcca

---

The invention claimed is:

1. A method for enriching target single-stranded nucleic acids in a mixed population of single-stranded nucleic acids, said method comprising:
   a) providing a mixed population of single-stranded nucleic acids containing target single-stranded nucleic acids and non-target single-stranded nucleic acids, wherein the target single-stranded nucleic acids comprise a target sequence at or within 21 bp of their 5' ends;
   b) contacting the mixed population of single-stranded nucleic acids with a blocking oligonucleotide, wherein the blocking oligonucleotide is capable of hybridising to the target sequence of the target single-stranded nucleic acids, resulting in the target nucleic acid lacking an affinity binding domain attached to a capture domain;
   c) contacting the mixed population of nucleic acids of step b) with a single-strand specific 5' exonuclease; and
   d) incubating the mixed population of nucleic acids of step c) under conditions for the 5' exonuclease to digest the non-target single-stranded nucleic acids, such that the target single-stranded nucleic acids are enriched,
   wherein the blocking oligonucleotide has a melting temperature (Tm) of at least 45° C., at least 47° C., or at least 49° C.

2. The method of claim 1, wherein the single-stranded nucleic acids are DNA or synthesized oligonucleotides.

3. The method of claim 1, wherein the mixed population of single-stranded nucleic acids is a library that comprises members that have repetitive sequences or members that share regions of sequence identity.

4. The method of claim 1, wherein the target single-stranded nucleic acids are from 50 to 1000 nucleotides in length, from 100 to 1000 nucleotides in length, or from 150 to 750 in nucleotides in length.

5. The method of claim 1, wherein the target sequence is from 10 to 50 nucleotides in length.

6. The method of claim 1, wherein the target sequence is located at the 5' end of target single-stranded nucleic acid.

7. The method of claim 1, wherein the blocking oligonucleotide is RNA.

8. The method of claim 1, further comprising the step of partially or completely eliminating the blocking oligonucleotide.

9. The method of claim 8, wherein eliminating is done by digesting the blocking oligonucleotide with a ribonuclease.

10. The method of claim 1, wherein the single-strand specific 5' exonuclease is an RecJ enzyme.

11. The method of claim 1, further comprising, after step d), the step of inactivating and/or removing the single-strand specific 5' exonuclease.

12. The method of claim 1, further comprising providing a single-stranded binding protein (SSBP).

13. The method claim 1, further comprising the step of incorporating the target single-stranded nucleic acids into a vector.

14. The method of claim 13, wherein the target single-stranded nucleic acids are converted to target double-stranded nucleic acids prior to incorporation into the vector.

15. The method of claim 13, wherein the target nucleic acids are to be incorporated into the vector using enzymatic assembly of overlapping DNA fragments.

16. The method of claim 13, wherein the target single- or double-stranded nucleic acids and vector have corresponding overlapping regions configured to permit incorporation of the target single- or double-stranded nucleic acids into the vector by enzymatic assembly of overlapping DNA fragments.

17. The method of claim 13, wherein incorporating includes the steps of:
   i) providing a linear double-stranded DNA vector which comprises sequences at its 5' and 3' ends that overlap with sequences at the 5' and 3' ends of the target single- or double-stranded nucleic acids;
   ii) contacting the linear double-stranded DNA vector with an exonuclease, which chews back the ends of the double-stranded DNA vector to produce a vector having single-stranded overhangs;
   iii) contacting said vector having single-stranded overhangs with the target single-stranded nucleic acids or target double-stranded nucleic acids having single-stranded overhangs;
   iv) annealing complementary sequences of the target single- or double-stranded nucleic acids and the overhangs of vector to form an annealed vector product;
   v) contacting said annealed vector product with a DNA polymerase that extends the 3' ends to fill gaps in the annealed product; and
   vi) contacting the product of step v) with a ligase to heal nicks.

* * * * *